United States Patent [19]
Wick et al.

[11] Patent Number: 6,063,604
[45] Date of Patent: May 16, 2000

[54] TARGET NUCLEIC ACID SEQUENCE AMPLIFICATION

[75] Inventors: James F. Wick, Franklin; Reinhold Mueller; Michele L. Blassak, both of Wauwatosa; Richard K. Wilkosz, New Berlin, all of Wis.

[73] Assignee: Molecular Biology Resources, Inc., Milwaukee, Wis.

[21] Appl. No.: 08/949,770

[22] Filed: Oct. 14, 1997

Related U.S. Application Data

[63] Continuation of application No. 08/617,045, Mar. 18, 1996, abandoned.

[51] Int. Cl.⁷ .............................. C12P 19/34; C12Q 1/68; C07H 21/02; C12N 15/00

[52] U.S. Cl. ............................ 435/91.2; 435/6; 536/23.1; 536/24.3; 935/76; 935/77; 935/78

[58] Field of Search .......................... 435/6, 91.2, 91.21; 536/22.1, 23.1, 24.3, 24.33

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 5,130,238 | 7/1992 | Malek et al. | 435/91 |
| 5,270,184 | 12/1993 | Walker et al. | 435/91.2 |
| 5,310,652 | 5/1994 | Gelfand et al. | 435/6 |
| 5,399,491 | 3/1995 | Kacian et al. | 435/91.21 |
| 5,407,800 | 4/1995 | Gelfand et al. | 435/6 |
| 5,409,818 | 4/1995 | Davey et al. | 435/91.21 |
| 5,422,252 | 6/1995 | Walker et al. | 435/91.2 |
| 5,455,166 | 10/1995 | Walker | 435/91.2 |
| 5,459,055 | 10/1995 | Jendrisak et al. | 435/199 |
| 5,470,723 | 11/1995 | Walker et al. | 435/91.2 |
| 5,480,784 | 1/1996 | Kacian et al. | 435/91.21 |
| 5,518,884 | 5/1996 | Spears et al. | 435/6 |
| 5,523,204 | 6/1996 | Singer et al. | 435/5 |
| 5,536,649 | 7/1996 | Fraiser et al. | 435/91.2 |
| 5,547,861 | 8/1996 | Nadeau et al. | 435/91.2 |
| 5,550,025 | 8/1996 | Walker | 435/6 |
| 5,591,609 | 1/1997 | Auerbach | 435/91.2 |
| 5,593,867 | 1/1997 | Walker et al. | 435/91.2 |
| 5,620,869 | 4/1997 | Woodard et al. | 435/91.1 |
| 5,624,825 | 4/1997 | Walker et al. | 435/91.2 |
| 5,631,147 | 5/1997 | Lohman et al. | 435/91.2 |
| 5,641,633 | 6/1997 | Linn et al. | 435/6 |
| 5,648,211 | 7/1997 | Fraiser et al. | 435/6 |
| 5,667,994 | 9/1997 | Dilly et al. | 435/91.2 |
| 5,744,311 | 4/1998 | Fraiser et al. | 435/6 |

FOREIGN PATENT DOCUMENTS

| | | |
|---|---|---|
| 0 624 643 A2 | 11/1994 | European Pat. Off. . |
| 0 669 402 A2 | 8/1995 | European Pat. Off. .......... C12Q 1/68 |
| 0 678 582 A1 | 10/1995 | European Pat. Off. . |
| 0 795 611 A1 | 3/1997 | European Pat. Off. . |
| 0 795 610 A1 | 9/1997 | European Pat. Off. . |

OTHER PUBLICATIONS

The Stratagene Catalog p. 38–39 (1988).
Barany, "The Ligase Chain Reaction in a PCR World", PCR Methods and Appl., 1:5–16 (1991).
Boyd, et al., "A human BRCA1 gene knockout", Nature, 375:541–542 (1995).
Castilla, et al., "Mutations in the BRCA1 gene in families with early–onset breast and ovarian cancer", Nature Genet., 8:387–391 (1994).
Easton, et al., "Breast and Ovarian Cancer Incidence in BRCAI–Mutation Carriers", A,. J. Hum. Genet., 56:265–271 (1995).
Fleischmann, et al., "Whole–Genome Random Sequencing and Assembly of Haemophilus influenzae Rd", Science, 269:496–512 (1995).
Ford, et al., "The genetics of breast and ovarian cancer", Brit. J. Cancer, 72:805–812 (1995).
Friedman et al., "Confirmation of BRCA1 by analysis of germline mutations linked to breat and ovarian cancer in ten families", Nature Genet., 8:399–404 (1994).
Guatelli, et al., "Isothermal, in vitro amplification of nucleic acids by a multienzyme reaction modeled after retroviral replication", Proc. Natl. Acad. Sci. (USA), 87:1874–1878 (1990).
Kievits, et al., "NASBA™ isothermal enzymatic in vitro nucleic acid amplification optimized for the diagnosis of HIV–1 infection", J. Virol. Methods, 35:273–286, (1991).
Kwoh, et al., "Transcription–based amplification system and detection of amplified human immunodeficiency virus type 1 with a bead–based sandwich hybridization format", Proc. Natl. Acad. Sci. (USA), 86:1173–1177, (1989).
Myers, et al., "Reverse Transcription and DNA Amplification by *Thermus thermophilus* DNA Polymerase", Biochemistry, 30:7661–7666, (1991).
Nowak, "Discovery of AT Gene Sparks Biomedical Research Bonanza", Science, 268:1700–1701 (1995).
Saiki, et al., "Primer–Directed Enzymatic Amplification of DNA with a Thermostable DNA Polymerase", Science, 239:487–491 (1998).
Savitsky, et al., "A Single Ataxia Telangiectasia Gene with a Product Similar to PI–3 Kinase", Science, 268:1749–1753 (1995).

(List continued on next page.)

*Primary Examiner*—W. Gary Jones
*Assistant Examiner*—Ethan Whisenant
*Attorney, Agent, or Firm*—Marshall, O'Toole, Gerstein, Murray & Borun

[57] ABSTRACT

A method is provided for the rapid, substantially isostatic, segregation and amplification of the sequence information of a target nucleic acid sequence positioned within a single- or double-stranded polynucleotide. The method is based on the serial generation of double-stranded DNA engineered to contain terminal nicking sites, nicking of those sites, and extensions from those nicks, thereby displacing any existing polynucleotides. Further provided is a method for detecting polynucleotides using the method of the invention. A kit combining the components commonly used in practicing the method of the invention is also provided.

32 Claims, 5 Drawing Sheets

OTHER PUBLICATIONS

Shattuck–Eidens, et al., "A Collaborative Survey of 80 Mutations in the BRCA1 Breast and Ovarian Cancer Susceptibility Gene", J.A.M.A., 273:535–541 (1995).

Simard, et al., "Common origins of BRCA1 mutations in Canadian breast and ovarian cancer families", Nature Genet., 8:392–398 (1994).

Spargo, et al., Abstract, "Thermophilic Strand Displacement Amplification" (undated).

Veres, et al., "The Molecular Basis of the Sparse Fur Mouse Mutation", Science, 237:415–417 (1987).

Walker, et al., "Strand displacement amplification—an isothermal, in vitro DNA amplification technique", Nucl. Acids Res., 20:1691–1696 (1992).

Walker, et al., "Isothermal in vitro amplification of DNA by a restriction enzyme/DNA polymerase system", Proc. Natl. Acad. Sci. (USA), 89:392–396 (1992).

Walker, et al., "Multiplex strand displacement amplification (SDA) and detection of DNA sequences from *Mycobacterium tuberculosis* and other mycobacteria", Nucl. Acids Res., 22:2670–2677 (1994).

Walker, "Empirical Aspects of Strand Displacement Amplification", PCR Methods and Appl., 3:1–6 (1993).

Walter, et al., "Strand displacment amplification as an in vitro model for rolling–circle replication: Deletion formation and evolution during serial transfer", Proc. Natl. Acad. Sci. (USA), 91:7937–7941 (1994).

Wu, et al., "The Ligation Amplification Reaction (LAR)—Amplification of Specific DNA Sequences Using Sequential Rounds of Template–Dependent Ligation", Genomics 4:560–569 (1989).

Zwadyk, Jr., et al., "Rendering of Mycobacteria Safe for Molecular Diagnostic Studies and Development of a Lysis Method for Strand Displacement Amplification and PCR", J. Clin. Microbiol., 32:2140–2146 (1994).

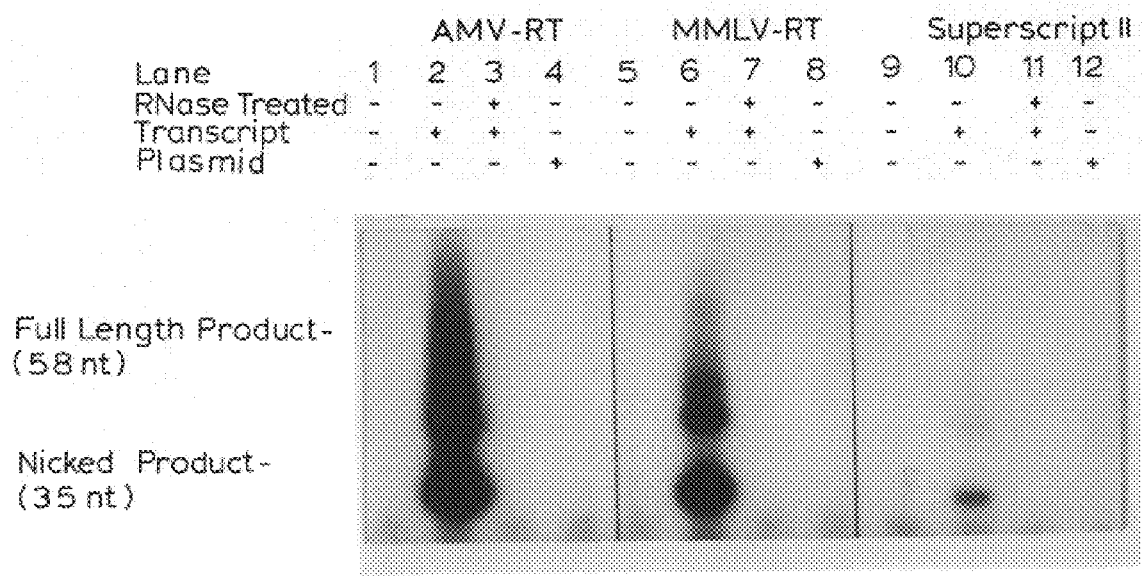

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1750 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: misc_feature
      (D) OTHER INFORMATION: /= "18s rRNA gene of Cryptosporidium parvum"

(xi) SEQUENCE DESCRIPTION: SEQ ID NO:1:

```
AACCTGGTTG ATCCTGCCAG TAGTCATATG CTTGTCTCAA AGATTAAGCC ATGCATGTCT      60

AAGTATAAAC TTTTATACGG TTAAACTGCG AATGGCTCAT TATAACAGTT ATAGTTTACT     120

TGATAATCTT TTACTTACAT GGATAACCGT GGTAATTCTA GAGCTAATAC ATGCGAAAAA     180

ACTCGACTTT ATGGAAGGGT TGTATTTATT AGATAAAGAA CCAATATAAT TGGTGACTCA     240
```

```
TAATAACTTT ACGGATCACA ATTAATGTGA CATATCATTC AAGTTTCTGA CCTATCAGCT      300

TTAGACGGTA GGGTATTGGC CTACCGTGGC AATGACGGGT AACGGGGAAT TAGGGTTCGA      360

TTCCGGAGAG GGAGCCTGAG AAACGGCTAC CACATCTAAG GAAGGCAGCA GGCGCGCAAA      420

TTACCCAATC CTAATACAGG GAGGTAGTGA CAAGAAATAA CAATACAGGA CTTTTTGGTT      480

TTGTAATTGG AATGAGTTAA GTATAAACCC CTTTACAAGT ATCAATTGGA GGGCAAGTCT      540

GGTGCCAGCA GCCGCGGTAA TTCCAGCTCC AATAGCGTAT ATTAAAGTTG TTGCAGTTAA      600

AAAGCTCGTA GTTGGATTTC TGTTAATAAT TTATATAAAA TATTTTGATG AATATTTATA      660

TAATATTAAC ATAATTCATA TTACTATTTT TTTTTTTAGT ATATGAAATT TTACTTTGAG      720

AAAATTAGAG TGCTTAAAGC AGGCATATGC CTTGAATACT CCAGCATGGA ATAATATTAA      780

AGATTTTTAT CTTTTTTATT GGTTCTAAGA TAAGAATAAT GATTAATAGG GACAGTTGGG      840

GGCATTTGTA TTTAACAGTC AGAGGTGAAA TTCTTAGATT TGTTAAAGAC AAACTAATGC      900

GAAAGCATTT GCCAAGGATG TTTTCATTAA TCAAGAACGA AAGTTAGGGG ATCGAAGACG      960

ATCAGATACC GTCGTAGTCT TAACCATAAA CTATGCCAAC TAGAGATTGG AGGTTGTTCC     1020

TTACTCCTTC AGCACCTTAT GAGAAATCAA AGTCTTTGGG TTCTGGGGGG AGTATGGTCG     1080

CAAGGCTGAA ACTTAAAGGA ATTGACGGAA GGGCACCACC AGGAGTGGAG CCTGCGGCTT     1140

AATTTGACTC AACACGGGAA AACTCACCAG GTCCAGACAT AGGAAGGATT GACAGATTGA     1200

TAGCTCTTTC TTGATTCTAT GGGTGGTGGT GCATGGCCGT TCTTAGTTGG TGGAGTGATT     1260

TGTCTGGTTA ATTCCGTTAA CGAACGAGAC CTTAACCTGC TAAATAGACA TAAGAAATAT     1320

TATATTTTTT ATCTGTCTTC TTAGAGGGAC TTTGTATGTT TAATACAGGG AAGTTTTAGG     1380

CAATAACAGG TCTGTGATGC CCTTAGATGT CCTGGGCCGC GCGCGCGCTA CACTGATGCA     1440

TCCATCAAGT ATATATTCCT GTTTCGAAGG AAATGGGTAA TCTTTTGAAT ATGCATCGTG     1500

ATGGGGATAG ATCATTGCAA TTATTGATCT TGAACGAGGA ATTCCTAGTA AGCGCAAGTC     1560

ATCAGCTTGC GCTGATTACG TCCCTGCCCT TTGTACACAC CGCCCGTCGC TCCTACCGAT     1620

TGAATGATCC GGTGAATTAT TCGGACCATA CTTTGTAGCA ATACATGTAA GGAAAGTTTC     1680

GTAAACCTTA TCATTTAGAG GAAGGAGAAG TCGTAACAAG GTTTCCGTAG GTGAACCTGC     1740

AGAAGGATCA                                                            1750
```

(2) INFORMATION FOR SEQ ID NO:2:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: /= "Primer P1"

(xi) SEQUENCE DESCRIPTION: SEQ ID NO:2:

```
ACCCCATCCA ATGCATGTCT CGGGTCGTAG TCTTAACCAT                              40
```

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single

```
        (D) TOPOLOGY: linear (ii) MOLECULE TYPE: DNA (ix) FEATURE:
        (A) NAME/KEY: misc_feature
        (D) OTHER INFORMATION: /= "Primer P2"

(xi) SEQUENCE DESCRIPTION: SEQ ID NO:3:

CGATTCGGCT CCAGACTTCT CGGGTGCTGA AGGAGTAAGG                                    40

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (D) OTHER INFORMATION: /= "Detection Probe"

(xi) SEQUENCE DESCRIPTION: SEQ ID NO:4:

AGAGATTGGA GGTTG                                                               15
```

TARGET NUCLEIC ACID SEQUENCE AMPLIFICATION

This is a continuation of U.S. application Ser. No. 08/617,045, filed Mar. 18, 1996, now abandoned.

FIELD OF THE INVENTION

The present invention is directed to a method for the exponential amplification of DNA or RNA that allows one to detect the presence of any target nucleic acid sequence in a mixture of polynucleotides using only two amplification primers under substantially isostatic conditions. The present invention is also directed to a method for generating the amplification intermediates of the target nucleic acid that are used in the amplification process. The present invention is useful because it permits the amplification and detection of any target nucleic acid sequence that is characteristic of any organism or genetic condition, even if present in minute quantities in a larger uncharacterized polynucleotide or in a mixture of polynucleotides. A particularly useful application of the method of the present invention is in testing food, biological fluids and water supplies for the presence of a target nucleic acid sequence that is characteristic of a pathogen, e.g., a virus, bacterium, parasite, or fungus capable of causing disease in humans, animals or plants.

BACKGROUND OF THE INVENTION

The amplification, detection and quantification of specific target nucleic acid sequences is useful in a variety of contexts, including microorganism classification, identification of genetic abnormalities including inborn errors of metabolism, diagnosis of infectious diseases, forensic analysis, environmental testing, and studies involving developmental and cellular biology.

The primary approach to polynucleotide detection involves discrimination based on sequence specificity. Typically, polynucleotide assays exploit the capacity of nucleic acids to hybridize or anneal in a sequence-specific (i.e., complementary) manner. The ability to detect polynucleotides by hybridization is dependent on the sensitivity of the assay. The sensitivity of these hybridization assays is a function of the specific activity of the probe system, comprising polynucleotides used to search for complementary sequences in a sample, along with any components used in signal generation. However, there are limits to the specific activity of a polynucleotide probe system. To further increase the sensitivity of hybridization assays, those of skill in the art have begun to increase the quantity of target nucleic acid sequence being assayed.

A variety of amplification techniques have been devised to improve the detection of nucleic acid targets by means of increasing the amount of the initial target molecule. These techniques include Strand Displacement Amplification (i.e., SDA), the Polymerase Chain Reaction (i.e., PCR), Reverse Transcription Polymerase Chain Reaction (i.e., RT-PCR), Nucleic Acid Sequence-Based Amplification (i.e., NASBA), Self-Sustained Sequence Replication (i.e., 3SR), and the Ligase Chain Reaction (i.e., LCR). Each of these techniques produces greater quantities of a target polynucleotide, thereby increasing the sensitivity of polynucleotide detection assays.

Strand Displacement Amplification (SDA) is described in Walker et al., *Proc. Natl. Acad. Sci.* (*USA*) 89:392–396 (1992), Walker et al., *Nucl. Acids Res.* 20(7):1691–1696 (1992), and U.S. Pat. Nos. 5,270,184, 5,422,252, 5,455,166, and 5,470,723. SDA is an isothermal amplification technique that generates DNA copies of a single- or double-stranded target polynucleotide fragment.

The original SDA methodology described in Walker et al., *Proc. Natl. Acad. Sci.* (*USA*) 89:392–396 (1992) and U.S. Pat. No. 5,455,166 discloses the amplification of the entire sequence of a single- or double-stranded target polynucleotide fragment. The technique employs two primers with each primer exhibiting a target binding region at its 3' terminus. Disposed towards the 5' terminus of each primer is a single-stranded sequence corresponding to a nickable restriction endonuclease recognition site. These recognition sequences are not necessarily complementary to any sequence in the target polynucleotide fragment, and are designed to overhang the 3' ends of an original double-stranded target polynucleotide fragment, or the 3' ends of an original single-stranded target polynucleotide and its complement. In these positions, the unbound sequences overhanging the 3' ends of the target polynucleotide and primer serve as templates for enzymatic extensions from the free 3' ends of both the primer and its target polynucleotide, respectively. Because these primers must overhang any 3' end of a target polynucleotide fragment (and the complement of the target), in order to create the required nickable site or sites (which must be double-stranded), the SDA method requires knowledge of the nucleotide sequence at both 3' ends of any double-stranded target polynucleotide fragment to be amplified. For the amplification of any single-stranded target polynucleotide, the nucleotide sequences of the 5' end and the 3' ends must be known. This is a difficult task if the sample to be analyzed contains a mixture of polynucleotide fragments from a variety of sources and in various stages of degradation or fragmentation, such as found in biological fluids, tissues, foods and water supplies. Accordingly, it is an object of the present invention to provide a method for amplification of a target nucleic acid sequence that does not require knowledge of the nucleotide sequence at the exact ends of the target polynucleotide fragment, suspected of containing the target nucleic acid sequence.

Improvements to the SDA method are described in U.S. Pat. Nos. 5,270,184 and 5,422,252. The '184 patent describes a method of amplification that involves four primers. In addition to the amplification primers ($S_1$ and $S_2$) that are used in the original SDA method, the method of the '184 patent includes two bumper primers ($B_1$ and $B_2$). To design the sequences of these four primers, the '184 method requires knowledge of the polynucleotide sequence at each end of an internal target nucleic acid sequence and, additionally, at regions flanking these terminal target sequences. These requirements present obstacles to amplification in terms of the time and effort required to sufficiently characterize the polynucleotide sequence of a targeted genomic region, such as a diagnostic portion of a pathogenic virus or a disease-linked genetic allele in humans. Additionally, the '184 method suffers from a heightened potential for artifactual and misleading results produced by spurious annealing of members of the required set of four primers.

Another improvement on the original SDA method involves "multiplex" amplification as described in the '252 and '723 patents. The method described in these patents, while allowing the simultaneous amplification of more than one target nucleic acid sequence, requires six primers (the two original SDA primers, two bumper primers, and two adapter primers) and a correspondingly greater characterization of the polynucleotide sequence of a target genome to construct the six primers than is demanded by the original SDA method or the method described in the '184 patent. Further, the greater number of primers in the reaction mixture increases the likelihood of competing amplification reactions. Accordingly, an object of the present invention is to limit the required characterization of a target genome to sequences at the termini of a target nucleic acid sequence sufficient to allow the binding of two primers under standard conditions in the art.

The Polymerase Chain Reaction (PCR) provides an alternative method for amplifying a target sequence found in a DNA molecule. Saiki et al., *Science* 239:487–491 (1989) and U.S. Pat. Nos. 4,683,195, 4,683,202 and 4,800,159. Although the PCR method only uses two primers, PCR is limited to amplifying defined regions of a target DNA and requires a thermocycling apparatus for practical implementation. Accordingly, it is an object of the present invention to provide a method that is not only capable of amplifying both target DNA and RNA, but also that does not require thermocycling or the use of thermocycling equipment.

RT-PCR is a modification of PCR that permits the amplification of a target sequence found in an RNA molecule. Myers et al., *Biochemistry* 30:7661–7666 (1991) and U.S. Pat. Nos. 5,310,652 and 5,407,800. In RT-PCR, the PCR cycle is preceded by the reverse transcription of an RNA target, thereby generating a cDNA product, which can then be amplified by PCR. Like PCR, RT-PCR only becomes practical with the automation of the requisite temperature changes, using a thermocycling apparatus. However, an object of the present invention is to provide a method for the amplification of a target polynucleotide that does not require thermocycling or thermocycling equipment.

Other amplification procedures that have been developed suffer from other shortcomings. Nucleic Acid Sequence Based Amplification (NASBA) and Self-Sustained Sequence Replication (3SR) will amplify RNA target molecules, producing primarily single-stranded RNA, with some single- and double-stranded DNA. NASBA is described by Kievits et al., *J. Virol. Methods* 35:273–286 (1991), and U.S. Pat. Nos. 5,130,238 and 5,409,818. 3SR is described by Guatelli et al., *Proc. Natl. Acad. Sci. (USA)* 87:1874–1878 (1990). A similar method is described in U.S. Pat. No. 5,399,491. These methods share several features, including the reverse transcription of an RNA target molecule, second-strand synthesis to yield double-stranded cDNA which contains a promoter introduced by an appropriately designed primer, and use of the promoter to generate RNA transcripts. The process relies on mesophilic microbial enzymes which are labile at elevated temperatures. This lability restricts the NASBA technique to maximum temperatures of approximately 41° C. At this relatively low temperature, however, the requisite primers exhibit reduced hybridization fidelity. Consequently, the technique suffers from background problems due to the frequent introduction of the promoter sequence, from the promoter-containing primer, at unintended locations, thereby creating promoters at unwanted positions. In addition, the techniques have been found to be extraordinarily sensitive to imbalances in reaction components, particularly the levels of enzyme activities. Moreover, the predominant product is RNA, a polynucleotide that is less stable than DNA.

Another method of nucleic acid sequence amplification is the Ligase Chain Reaction (LCR), first developed by Wu et al., *Genomics* 4:560–569 (1989); a thermophilic version was introduced by Barany, *PCR Methods and Applications* 1:5–16 (1991). LCR employs two pairs of primers. In LCR, one pair of primers anneals to adjacent positions on a target nucleic acid sequence. The other pair of primers anneals to adjacent positions on the complement of the target nucleic acid sequence region that binds the first set of primers. Although the target in LCR is amplified exponentially, the method lacks fidelity because of a tendency to produce target-independent ligations. Moreover, the amplified products consist almost entirely of pre-existing primer sequences. In addition, LCR, like PCR, requires thermocycling and the thermocycling instrumentation that brings practicality to the method. Accordingly, an object of the present invention is not only to eliminate the need for thermocycling and four primers, but also to provide a method wherein the amplified product is not dominated by pre-existing primer sequences.

Therefore, a need exists in the art for a versatile, reliable, and simple method for nucleic acid sequence amplification. Such a method should be capable of amplifying both DNA and RNA and should do so exponentially, using a minimum number of primers under substantially isostatic conditions.

SUMMARY OF THE INVENTION

The present invention satisfies the aforementioned needs by providing a method and kit for amplifying nucleic acid sequences using enzyme-catalyzed extensions from two amplification primers under substantially isostatic conditions of substantially constant temperature and reagent concentrations. One aspect of the present invention involves a method for segregating, between two hemi-modified restriction endonuclease recognition sites, a copy of a target nucleic acid sequence from a substantially larger polynucleotide, the method being applicable to both RNA and DNA and to single- and double-stranded targets. Where the target nucleic acid sequence is considered to be a single-stranded nucleic acid sequence, it is understood that both a copy of the target nucleic acid sequence and its complement are segregated between the two hemi-modified restriction endonuclease recognition sites. A single-stranded polynucleotide is obtained from a single-stranded polynucleotide or a double-stranded polynucleotide by standard techniques in the art. A second aspect of the present invention is directed to a method for amplifying the segregated copy of the target nucleic acid sequence in the presence of two primers that define the opposing ends of a target nucleic acid sequence, if present, and provide for exponential amplification of the segregated copy, relatively free from undesired dominating side reactions. Further, it is within the scope of the present invention that the first and second aspects be carried out separately, or simultaneously in the same reaction mixture.

In particular, in its first aspect, the present invention is directed to a method for segregating a copy of a target nucleic acid sequence located within a single-stranded polynucleotide, the segregated copy suitable for use in amplifying the target nucleic acid sequence, the method comprising:

(a) hybridizing a first amplification primer to the 3' end of a target nucleic acid sequence within a single-stranded polynucleotide to form a hybridized first amplification primer, the first amplification primer comprising an oligodeoxyribonucleotide having a 3' end and a 5' end, the 3' end of the first amplification primer being complementary to the 3' end of the target nucleic acid sequence, the 5' end of the first amplification primer having a first recognition sequence for a first restriction endonuclease that is capable of nicking one strand of a double-stranded hemi-modified recognition site for the first restriction endonuclease;

(b) extending the hybridized first amplification primer along its 3' end in the presence of deoxyribonucleoside triphosphates, a modified deoxyribonucleoside triphosphate, and a first polymerizing enzyme capable of polymerizing deoxyribonucleoside triphosphates using the target nucleic acid sequence as a template to produce a first double-stranded polynucleotide having a first modified polynucleotide extension product that is complementary and bound to the single-stranded polynucleotide;

(c) separating the single-stranded polynucleotide from the first modified polynucleotide extension product;

(d) hybridizing a second amplification primer to an internal site on the first modified polynucleotide extension product to form a hybridized second amplification primer, the second amplification primer comprising an oligodeoxyribonucleotide having a 3' end and a 5' end, the 3' end of the second amplification primer being complementary to the 3' end of the complement of the target nucleic acid sequence and capable of hybridizing thereto, the 5' end of the second amplification primer having a second recognition sequence for a second restriction endonuclease that is capable of nicking one strand of a double-stranded hemi-modified recognition site for the second restriction endonuclease;

(e) extending the hybridized second amplification primer along its 3' end in a reaction mixture comprising a mixture of deoxyribonucleoside triphosphates, a modified deoxyribonucleoside triphosphate, and a second polymerizing enzyme capable of polymerizing deoxyribonucleoside triphosphates in the presence of a polynucleotide template and capable of strand displacement, to produce a second double-stranded polynucleotide comprising a second modified polynucleotide extension product that is hybridized to the first modified polynucleotide extension product, the second modified polynucleotide extension product comprising a copy of the target nucleic acid sequence segregated from the single-stranded polynucleotide and positioned at opposing ends between the second recognition sequence and the complement of the first recognition sequence, the first recognition sequence on the first modified polynucleotide extension product and the complement of the first recognition sequence on the second polynucleotide extension product forming a double-stranded hemi-modified recognition site for the first restriction endonuclease; and (f) nicking one strand of the double-stranded hemi-modified recognition site for the first restriction endonuclease in the presence of the first restriction endonuclease, deoxyribonucleoside triphosphates, a modified deoxyribonucleoside triphosphate, and the second polymerizing enzyme, whereby the 3' end produced by the nick is extended, thereby displacing any portion of the first modified polynucleotide extension product downstream therefrom and forming a third double-stranded polynucleotide comprising a segregated copy of the target nucleic acid sequence that is hybridized to a segregated copy of the complement of the target nucleic acid sequence, the third double-stranded polynucleotide being defined at opposing ends by the first nickable recognition site and a second nickable recognition site for the first and second restriction endonucleases, respectively.

The above-described method of segregating an amplifiable copy of a target nucleic acid sequence that is found within a single-stranded polynucleotide may conveniently be performed in a single reaction mixture containing all of the reactants mentioned therein. In this latter and preferred embodiment, all of the above-mentioned hybridizing, extending, and nicking steps occur spontaneously in the reaction mixture with no active steps required other than providing the reaction mixture. However, to provide a single-stranded nucleic acid substrate for the spontaneous hybridizing, extending, and nicking steps of the above-described process, the reaction mixture containing or suspected of containing a single-stranded polynucleotide of interest must be subjected to at least one separating step wherein any double-stranded nucleic acids in the reaction mixture are separated into single-stranded nucleic acids capable of hybridizing with the appropriate target-seeking primer, which is then extended in the 3' direction across the target template.

Accordingly, when the preferred embodiment of the Applicants' method of segregating a copy of a target nucleic acid sequence is expressed in terms of its active steps, it is substantially shorter than Applicants' first-described embodiment. Thus, Applicants' preferred embodiment is directed to a method for segregating a copy of a target nucleic acid sequence found within a single-stranded polynucleotide, the segregated copy suitable for use in amplifying the target nucleic acid sequence, the method comprising:

(a) providing a reaction mixture comprising:

(i) a sample containing or suspected of containing a target nucleic acid sequence positioned within a single-stranded polynucleotide at other than an end of the polynucleotide;

(ii) a first polymerizing enzyme capable of polymerizing deoxyribonucleoside triphosphates by extending a hybridized primer, using the single strand of the polynucleotide as a template, and a second polymerizing enzyme capable of polymerizing deoxyribonucleoside triphosphates by extending a hybridized primer and capable of strand displacement, with the proviso that when the target nucleic acid is a DNA, the first polymerizing enzyme is optionally the same as the second polymerizing enzyme;

(iii) a mixture of deoxyribonucleoside triphosphates that includes a modified deoxyribonucleoside triphosphate;

(iv) a first amplification primer capable of hybridizing to the target nucleic acid sequence and forming a hybridized primer therewith, the first amplification primer comprising an oligodeoxyribonucleotide having a 3' end and a 5' end, the 3' end of the first amplification primer being complementary to the 3' end of the target nucleic acid sequence, the 5' end of the first amplification primer having a first recognition sequence for a first restriction endonuclease that is capable of nicking one strand of a double-stranded hemi-modified recognition site for the first restriction endonuclease; and (v) a second amplification primer comprising an oligodeoxyribonucleotide having a 3' end and a 5' end, the 3' end of the second amplification primer being complementary to the 3' end of the complement of the target nucleic acid sequence and capable of hybridizing thereto, the 5' end of the second amplification primer having a second recognition sequence for a second restriction endonuclease that is capable of nicking one strand of a double-stranded hemi-modified recognition site for the second restriction endonuclease;

(b) subjecting the reaction mixture to a means for separating any double-stranded nucleic acid in the reaction mixture into single strands; and (c) allowing the reaction mixture sufficient time for hybridization, primer extension, and nicking to occur, whereby there is produced a double-stranded polynucleotide extension product suitable for amplification comprising a segregated copy of the target nucleic acid sequence and a segregated copy of the complement of the target nucleic acid sequence, the double-stranded polynucleotide extension product being defined at opposing ends by a first nickable restriction site and a second nickable restriction site for the first and second restriction endonucleases, respectively.

The above-described method is referred to hereinafter as "the short segregation method, steps (a)–(c)."

In its second aspect, the present invention is directed to a method for amplification of a target polynucleotide that utilizes the segregated copy of the target nucleic acid sequence, as obtained above, as an intermediate, i.e., as an amplification template, in a polynucleotide amplification reaction scheme. Accordingly, the second aspect of the present invention is directed to a method for amplifying a target nucleic acid sequence within a mixture of polynucleotides, the method comprising steps (a)–(f) above and further including:

(g) amplifying the segregated copy of the target nucleic acid sequence or its complement by contacting the third double-stranded polynucleotide with the first restriction endonuclease and the second restriction endonuclease in the presence of a mixture of an enzyme having a DNA polymerase activity and capable of strand displacement, deoxyribonucleoside triphosphates, and a modified deoxyribonucleoside triphosphate, whereby the first and second recognition sequences of the first and the second recognition sites are nicked and the 3' ends of the sites that are nicked are extended, generating a nascent target nucleic acid sequence or its complement, and displacing the downstream copy of the target nucleic acid sequence or its complement in the process; and (h) allowing step (g) to continue for a sufficient time to produce a detectable amount of the segregated copies of the target nucleic acid sequence.

Alternatively, the method of amplifying a target nucleic acid sequence that is located within a polynucleotide sequence is performed by taking steps (g) and (h) above and adding them as steps (d) and (e), respectively, to the short segregation method, steps (a)–(c), with one modification to the language of each one of steps (g) and (h). First, the step (g) reference to "contacting the third double-stranded polynucleotide" is replaced in step (d) by "contacting the double-stranded polynucleotide extension product." Second, the step (h) reference to "step (g)" is replaced in step (e) by a reference to "step (d)." The method of amplification of this paragraph is referred to hereinafter as "the short amplification method, steps (a)–(e)."

In a third aspect of the present invention, the presence of amplified copies of the segregated target nucleic acid sequence is determined using conventional DNA detection and characterization techniques, whereby detection of the segregated target nucleic acid sequence, e.g., a species-specific genotype characterized by the target nucleic acid sequence, identifies the genotype of an organism or reflects that a particular organism was in or had contact with a sample that was tested. Thus, a method of determining the presence of a detectable amount of a segregated copy of the target nucleic acid sequence, e.g., whether a sample of interest is associated with a particular genotype or organism, includes steps (a)–(h) above and as step (i):

(i) determining the presence of the detectable amount of the segregated copies of the target nucleic acid sequence whereby the presence of a detectable amount of the target nucleic acid sequence indicates the presence in the sample of the genotype or organism associated with the target nucleic acid sequence.

In an alternative embodiment, the method of determining the presence of the target nucleic acid sequence comprises taking step (i) from above and adding it as step (f) to the short amplification method, steps (a)–(e). This latter method of determining the presence of a detectable amount of target nucleic acid sequence is referred to hereinafter as "the short determining method, steps (a)–(f)."

In a preferred embodiment, the polynucleotide portions of the amplicon (i.e., copied, or amplified strands) that are complementary to each primer are modified because those polynucleotide portions were synthesized using modified deoxyribonucleoside triphosphates. Consequently, terminally located restriction endonuclease recognition sites are substantially hemi-modified, containing, in the regions of the terminal recognition sites, a substantially unmodified nucleotide composition contributed by the primer itself and a modified complementary strand. As substantially hemi-modified sites, these restriction sites can be made nickable (i.e., amenable to single-strand cleavage) by, e.g., ensuring that the nucleotide immediately 3' to the cleavage position on one strand of the site is modified.

The restriction endonuclease recognition sites at each end of the double-stranded polynucleotide may be designed for different restriction endonucleases. The nickable restriction endonuclease recognition sites may be nicked by one or more appropriate restriction endonucleases. If more than one nicking enzyme is used, moreover, one of the enzymes may be selectively inactivated at some point during the method of amplification, for example by heat or chelation of a required metal cofactor. Alternatively, different amounts of each enzyme may be added to the reaction. Consequently, the method may yield an asymmetric amplification of one strand. Another enzyme, possessing a polymerase activity, being capable of strand displacement and preferably lacking effective exonuclease activity, extends the internal 3' termini produced by nicking each of the terminal restriction endonuclease recognition sites. The polynucleotide syntheses extending from the nicks displace the existing polynucleotide strands that terminated at the internal 5' termini generated by the nicking events. The sequence information of the segregated target nucleic acid sequence is amplified by repeating the nicking, extending and displacing steps.

This third aspect of the invention is utilized to amplify a target DNA or RNA that is associated with a particular condition and, additionally, to determine the existence of that condition based on considerations that include, but are not limited to, detecting the presence of a target polynucleotide associated with a condition.

In a preferred embodiment, the method according to the invention is used to determine the presence of *Cryptosporidium parvum* in environmental water based upon segregation and amplification of a target nucleic acid sequence, if present, that characterizes *C. parvum*. In another preferred embodiment of the method, the potential development of a disease condition is assessed. For example, the method can be used to detect particular genetic alleles associated with human breast cancer. In another embodiment, the method of the present invention can be used to rapidly detect the presence of Salmonella spp., Clostridium spp. (e.g., *C. botulinum* or *C. perfringens*), and other bacterial species in processed foods, meats and dairy products. Beyond these examples, the method can be used to detect the nucleic acids of disease-causing viruses in humans, other animals, and plants.

Another aspect of the invention is directed to a kit including components for practicing the method of the invention, comprising:

(a) a polymerizing enzyme capable of polymerizing deoxyribonucleoside triphosphates to generate a first product consisting essentially of a complement of a template, the enzyme being capable of strand displacement;

(b) a pair of amplification primers comprising a first amplification primer and a second amplification primer, the first amplification primer having a 3' end that is complementary to the 3' end of a target nucleic acid sequence that is positioned within a larger polynucleotide at a location other than a terminus, and a 5' end that includes a first recognition sequence for a first restriction endonuclease capable of nicking a hemi-modified first recognition site, the second amplification primer having a 3' end that is complementary to the 3' end of the complement of the target nucleic acid sequence and a 5' end that includes a second recognition sequence for a second restriction endonuclease capable of nicking a hemi-modified second recognition site;

(c) from one to two restriction endonucleases capable of nicking a substantially hemi-modified restriction endonuclease recognition site;

(d) deoxyribonucleoside triphosphates; and (e) a modified deoxyribonucleoside triphosphate.

As would be understood by one of skill in the art, additional components may be added to the kit, for example buffers and/or a polynucleotide strand separating means, for example, a means comprising an RNase H activity, without exceeding the scope of the present invention.

A distinct advantage accruing from practice of the present invention relates to the ability to amplify any target nucleic acid sequence when present in a larger single-stranded polynucleotide and, further, when that polynucleotide is present in a mixture of polynucleotides and/or polynucleotide fragments. This versatile amplification capacity permits the entire sequence, or any subsequence, of any polynucleotide to be amplified. This versatility provides flexibility in designing amplification strategies and virtually eliminates the time and expense previously required to generate target polynucleotides whose full length was suitable for amplification.

Another advantage of the present invention relates to the ability to amplify polynucleotide sequences under substantially isostatic conditions. The substantially isostatic conditions comprise a substantially constant temperature and a substantially unmodified reaction composition. Although initial steps in the method of the present invention may involve temperature changes to obtain denaturations of double-stranded polynucleotide fragments containing or suspected of containing target nucleic acid sequences, or of single-stranded target polynucleotides hybridized to a first polynucleotide extension product, the later amplification cycles do not involve temperature changes. Moreover, in some embodiments of the invention, such as where the target polynucleotide is single-stranded, e.g., RNA, the need to change the reaction temperature is further reduced. Also, reactants are continuously converted to products during the amplification reaction. However, isostatic conditions are maintained because there is no need to adjust reagent quantities at any time after reaction initiation. Moreover, because the reaction volume is not varied, reagent concentrations are not adjusted by direct, or indirect, operator intervention. Thus, the method of the present invention proceeds to completion without the costly requirements for ongoing monitoring or manipulation.

Yet another advantage of the method of the present invention is the ability to amplify any polynucleotide sequence using two primers. The present invention incorporates the sequences of these primers into amplification intermediates without further need for adapter, bumper, or ligation primers. Because primers are routinely generated by costly synthetic routes, this minimization of primers necessary for amplification according to the invention reduces the cost of practicing the present invention.

Numerous aspects and advantages of the present invention will be apparent upon consideration of the following drawings and detailed description.

BRIEF DESCRIPTION OF THE DRAWINGS

FIG. 2 depicts an autoradiogram of gel-fractionated products from probe-extension assays using three reverse transcriptases—AMV-RT (Lanes 1–4), MMLV-RT (Lanes 5–8), and Superscript II (Lanes 9–12).

DETAILED DESCRIPTION OF THE INVENTION

Figure 1A:
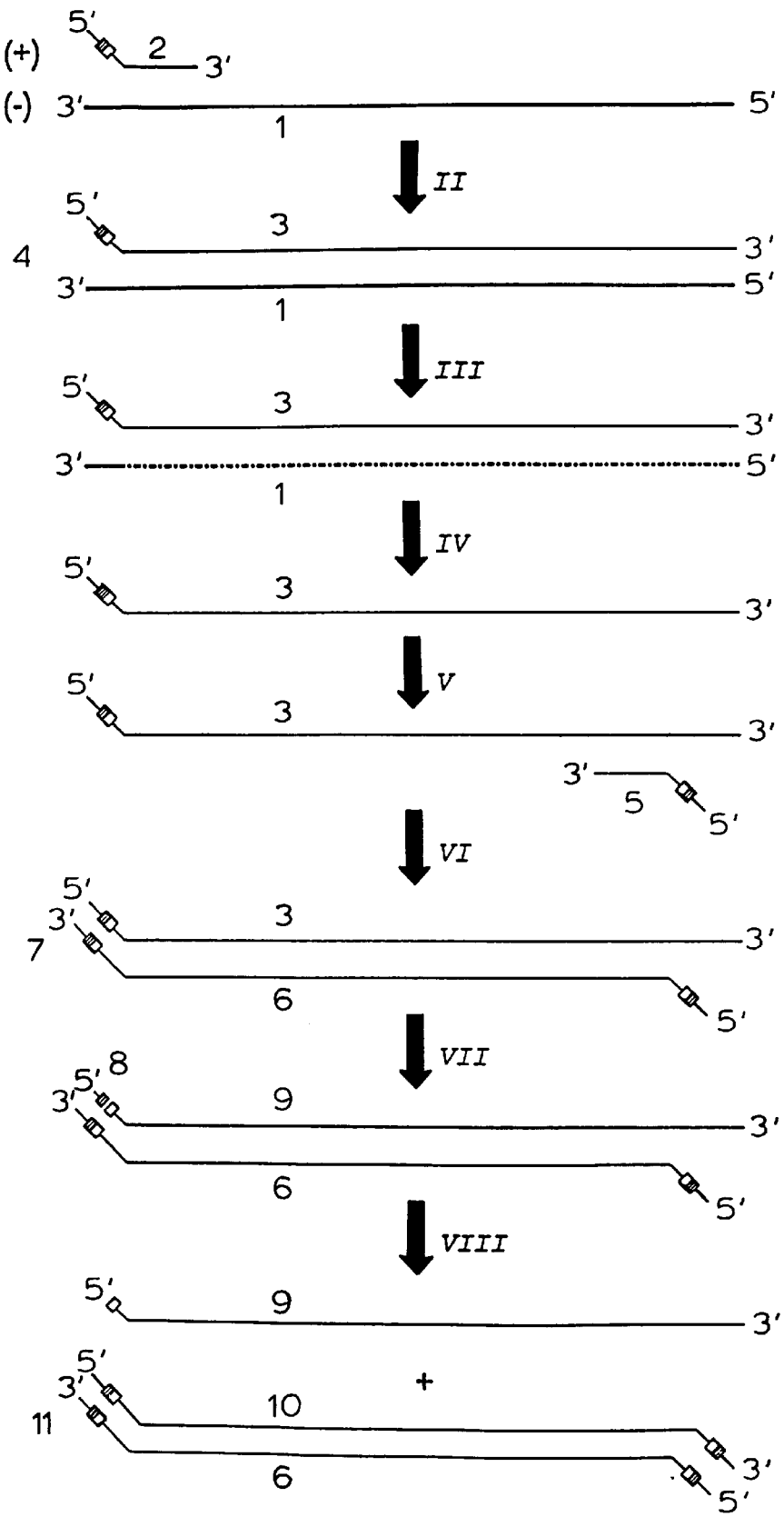
FIGS. 1a–1b schematically illustrates a method according to the invention.

The present invention has multiple aspects. In one aspect, the present invention is directed to a method of segregating a copy of a target nucleic acid sequence from a single-stranded polynucleotide using two amplification primers and substantially isostatic conditions, wherein the copy (and its complement) is segregated between two hemi-modified restriction endonuclease recognition sites to provide a readily amplifiable copy of the target nucleic acid sequence substantially free of non-target DNA. The single-stranded polynucleotide containing the target sequence is capable of being derived from a polynucleotide that is single stranded or from a double-stranded polynucleotide fragment or a mixture thereof by techniques that are known in the art.

In particular, in its first aspect, the present invention is directed to a method for segregating a copy of a target nucleic acid sequence located within a single-stranded polynucleotide, the segregated copy suitable for use in amplifying the target nucleic acid sequence, the method comprising:

(a) hybridizing a first amplification primer to the 3' end of a target nucleic acid sequence within a single-stranded polynucleotide to form a hybridized first amplification primer, the first amplification primer comprising an oligodeoxyribonucleotide having a 3' end and a 5' end, the 3' end of the first amplification primer being complementary to the 3' end of the target nucleic acid sequence, the 5' end of the first amplification primer having a first recognition sequence for a first restriction endonuclease that is capable of nicking one strand of a double-stranded hemi-modified recognition site for the first restriction endonuclease;

(b) extending the hybridized first amplification primer along its 3' end in the presence of deoxyribonucleoside triphosphates, a modified deoxyribonucleoside triphosphate, and a first polymerizing enzyme capable of polymerizing deoxyribonucleoside triphosphates using the target nucleic acid sequence as a template to produce a first double-stranded polynucleotide having a first modified polynucleotide extension product that is complementary and bound to the single-stranded polynucleotide;

(c) separating the single-stranded polynucleotide from the first modified polynucleotide extension product;

(d) hybridizing a second amplification primer to an internal site on the first modified polynucleotide extension product to form a hybridized second amplification primer, the second amplification primer comprising an oligodeoxyribonucleotide having a 3' end and a 5' end, the 3' end of the second amplification primer being complementary to the 3' end of the complement of the target nucleic acid sequence and capable of hybridizing thereto, the 5' end of the second amplification primer having a second recognition sequence for a second restriction endonuclease that is capable of nicking one strand of a double-stranded hemi-modified recognition site for the second restriction endonuclease;

(e) extending the hybridized second amplification primer along its 3' end in a reaction mixture comprising a mixture of deoxyribonucleoside triphosphates, a modified deoxyribonucleoside triphosphate, and a second polymerizing enzyme capable of polymerizing deoxyribonucleoside triphosphates in the presence of a polynucleotide template and capable of strand displacement, to produce a second double-stranded polynucleotide comprising a second modified polynucleotide extension product that is hybridized to the first modified polynucleotide extension product, the second modified polynucleotide extension product comprising a copy of the target nucleic acid sequence segregated from the single-stranded polynucleotide and positioned at opposing ends between the second recognition sequence and the complement of the first recognition sequence, the first recognition sequence on the first modified polynucleotide extension product and the complement of the first recognition sequence on the second polynucleotide extension product forming a double-stranded hemi-modified recognition site for the first restriction endonuclease; and (f) nicking one strand of the double-stranded hemi-modified recognition site for the first restriction endonuclease in the presence of the first restriction endonuclease, deoxyribonucleoside triphosphates, a modified deoxyribonucleoside triphosphate, and the second polymerizing enzyme, whereby the 3' end produced by the nick is extended, thereby displacing any portion of the first modified polynucleotide extension product downstream therefrom and forming a third double-stranded polynucleotide comprising a segregated copy of the target nucleic acid sequence that is hybridized to a segregated copy of the complement of the target nucleic acid sequence, the third double-stranded polynucleotide being defined at opposing ends by the first nickable recognition site and a second nickable recognition site for the first and second restriction endonucleases, respectively.

The term "target nucleic acid sequence" or "target sequence," as used herein, refers to a nucleic acid sequence of interest that is known or suspected of being within a larger polynucleotide that extends beyond both the 5' and 3' ends of the target sequence. In a typical polynucleotide contemplated for use in the present invention, the polynucleotide extends from one to thousands of bases beyond one or both of the 5' and 3' ends of the target, more typically, from more than ten to thousands of bases and occasionally greater than one thousand bases from both the 5' and 3' ends of the target nucleic acid sequence. Those skilled in the art recognize that the size of the polynucleotide containing the target sequence depends upon the size of the genome of interest and the degree of degradation or fragmentation of the polynucleotide (i.e., DNA or RNA) contained in any sample. Accordingly, the term "polynucleotide", as used herein, encompasses polynucleotide fragments. Target nucleic acid sequences that are suitable for use in the present invention include single-stranded RNA, double-stranded RNA, single-stranded DNA, double-stranded DNA, and a DNA-RNA duplex. However, in order to obtain hybridization of the first and second amplification primers, any double-stranded polynucleotides must be converted into their corresponding single-stranded components. The polynucleotide containing the target nucleic acid sequence is typically presented in a sample containing a plurality of other polynucleotides, many of which do not contain the target sequence. A target nucleic acid sequence is typically a sequence that is characteristic of a particular organism, animal, plant, bacterium, fungus, parasite, or virus. It may also be selected to distinguish, for example, organisms of the same species from one another, or to distinguish one strain of the same bacterium from another, or to distinguish genetic variations, for example mutations. Preferred target nucleic acid sequences are sequences associated with, and characteristic of, pathogenic organisms, such as pathogenic bacteria, viruses, molds, parasites, and fungi, as found in biological fluids, tissues, foods, and water supplies.

Examples of pathogenic bacteria capable of providing a target nucleic acid sequence suitable for amplification and detection by the method of the present invention include *Bacillus anthracis, Bacillus botulinus* (*Clostridium botulinum*), *Bacillus dysenterea, Bacillus enteritidis* (*Salmonella enteritidis*), *Bacillus pneumoniae* (*Diplococcus pneumoniae, Klebsiella pneumoniae*), *Bacillus tetani* (*Clostridium tetani*), *Bacillus typhosus* (*Salmonella typhosa*), *Chlamydia oculogenitalis, Clostridium perfringens, Hemophilus influenzae, Hemophilus pertussis, Mycobacteria tuberculosis, Neisseria gonorrhoeae, Pseudomonas aeruginosa, Shigella paradysenteriae, Staphylococcus aureus, Streptococcus agalactiae, Streptococcus faecalis, Streptococcus hemolyticus, Streptococcus mitis, Streptococcus pyrogenes, Vibrio cholerae, Vibrio comma, Vibrio fetus, Vibrio jejuni, Vibrio metchnikovii,* and *Vibrio niger.* Nucleic acid sequences characteristic of each of these species are known to the art and suitable for use in whole or part as target nucleic acid sequences in the method of the present invention. For example, the sequence of the complete genome of *H. influenzae* has been reported in Fleischmann et al., Science 269:496–512 (1995), which is incorporated herein by reference in its entirety.

Examples of viruses, including retroviruses, capable of providing a target nucleic acid sequence for amplification and detection by the method of the present invention include HSV-I, HSV-II, HIV, CMV, measles, polio, hepatitis B, hepatitis C, influenza, and the like. Nucleic acid sequences characteristic of each of these species are known to the art and suitable for use in whole or part as target nucleic acid sequences in the method of the present invention. See, e.g., *Molecular Methods for Virus Detection* (Danny L. Wiedbrauk and Daniel H. Farkas eds., AACC Press, Washington, D.C., 1995), which is incorporated herein by reference in its entirety.

The method of the present invention segregates target nucleic acid sequences or target sequences and enzymatically amplifies (i.e., copies) the sequence information contained in those targets using two amplification primers under substantially isostatic conditions of substantially constant temperature and reagent composition. Each of the two amplification primers contains a polynucleotide binding region located towards its 3' terminus and a single strand of a nickable restriction endonuclease recognition site (i.e., a recognition sequence) located towards its 5' terminus. The target nucleic acid sequence within a single-stranded polynucleotide is exploited as a template for primer-directed DNA synthesis. The two strands of the nascent duplex can then be separated and each strand used as an independent template, with each strand annealing to one of the two primers in the method of the invention. Alternatively, the single-stranded polynucleotide containing the original target polynucleotide can be destroyed and its surviving complement used as a template to synthesize a DNA copy of the target nucleic acid sequence. Only a few cycles are necessary to generate a double-stranded DNA containing nickable restriction endonuclease recognition sites at its termini.

The first and second nickable restriction endonuclease recognition sites may be the same or different. Further, the sites may be rendered nickable by using unmodified primers and performing the primer extension reactions in the presence of at least one modified deoxyribonucleoside triphosphate. Alternatively, the duplex polynucleotide can be subjected to strand-specific modification using techniques known in the art that result in a modified strand that, itself, cannot be cleaved.

Once a double-stranded, segregated DNA copy of the target nucleic acid sequence, flanked by nickable sites, has been produced, amplification proceeds under substantially isostatic conditions of temperature and reagent composition. Initially, each terminus of the duplex polynucleotide is nicked and the free 3' termini produced by the nicks are extended by a polymerizing enzyme capable of strand displacement. Preferably, the polymerizing enzyme is a DNA polymerase which displaces rather than destroys the pre-existing polynucleotide strands. The displaced strands anneal to additional complementary amplification primers and provide the opportunity for a geometric increase in the rate of amplification. The nicking, extending, and displacing steps are repeated, for example using a single reaction vessel not requiring repeated operator intervention.

Samples containing polynucleotides that are known or suspected of having a target nucleic acid sequence are obtained from an organism of interest or an environment known or suspected to have been in contact with the organism. Typical sources of samples containing or suspected of containing a target nucleic acid sequence from humans or animals are biological fluids, such as blood, saliva, tears, cerebrospinal fluid, effusions, exudates, urine, ascites fluid, sputum, mucous, semen, bone marrow, stools, and the like; or tissues such as lung, liver, kidney, spleen, heart, hair, skin and the like. Other sources of target nucleic acid sequences are plants, soils, foods (particularly meats, prepared foods, shellfish and dairy products) and water.

In a preferred embodiment, a target nucleic acid sequence comprises a nucleic acid sequence of *Cryptosporidium parvum*. More preferred is a polynucleotide sequence of the 18S rRNA gene of *C. parvum*. The nucleotide sequence of the *C. parvum* 18S rRNA gene is 1750 nucleotides and is available from the GenBank database under accession number L16997. The sequence of the *C. parvum* 18S rRNA gene is presented in SEQ ID NO:1. Typical samples that are analyzed for *C. parvum* include drinking water, surface water, and stool samples.

By the term "amplification primer," as used herein, is meant an oligodeoxyribonucleotide primer for the amplification, by primer extension, of a target nucleic acid sequence positioned within a larger polynucleotide. The 3' end of the amplification primer hybridizes at the 3' end of either the target nucleic acid sequence or its complement. The 5' end of the amplification primer does not necessarily hybridize to the original polynucleotide strand as found, e.g., in a sample, when the 3' end of the amplification primer is hybridized to that strand. In addition, the 5' end of the amplification primer includes, at a minimum, a recognition sequence for a restriction endonuclease or restriction enzyme. The recognition sequence is for a restriction endonuclease which will "nick" one strand of a DNA duplex when the recognition site is hemi-modified. By the term "nick," as used herein, is meant that only one of the two strands of a hemi-modified recognition site in a DNA duplex is cleaved—"nicked"—by the restriction endonuclease.

The present invention employs two amplification primers—a first amplification primer and a second amplification primer having first and second recognition sequences, respectively, for one or more restriction enzymes. It is within the scope of the present invention that the first and second recognition sequences be the same or different such that they are recognized and nickable by the same or different restriction enzymes. In addition, it is within the scope of the present invention that the amplification primers have one or more recognition sequences for additional restriction endonuclease recognition sites. For example, an additional recognition sequence positioned 5' to the recognition sequence for the nicking restriction endonuclease provides for subsequent cloning of a polynucleotide fragment comprising a double-stranded form of a segregated copy of a target nucleic acid sequence flanked by nickable recognition sites.

The polynucleotide binding region or target binding region of the primers must be sufficient to ensure effective annealing of the primers to the target nucleic acid sequence under the conditions used in executing the methods of the invention (see below) and in view of the potentially unhybridized portion of each primer containing the single strand of sequence information corresponding to a nickable restriction endonuclease recognition site. Preferably, the target binding portion of the primer will be at least about 16 nucleotides and the target binding site will involve at least about 40% of the primer nucleotides.

Preferred amplification primers are oligodeoxyribonucleotides lacking any nucleotides that, in a double-stranded molecule, would inhibit restriction endonuclease cleavage of a nicking site (i.e., an endonuclease recognition or restriction site designed to be nicked) by an enzyme capable of nicking a duplex polynucleotide. Thus, preferred primers of the invention may include modified nucleotides, provided those modified nucleotides would not inhibit cleavage of the primer polynucleotide at a nicking site by an enzyme with nicking activity when the primer is participating in a properly formed duplex polynucleotide.

Preferably, when introducing nickable sites recognized by different restriction endonucleases, the different restriction endonucleases can be selectively inactivated, for example by heat or metal chelation. An example involves a primer specifying one strand of the recognition site for BsiHKCI; a second primer specifies one strand of the recognition site for AlwI. Because AlwI is denatured by incubation for 20 minutes at 65° C. and BsiHKCI is not, one of the two nicking enzymes can be selectively denatured by exposing the amplification reaction to 65° C. for 20 minutes. Such reactions will then asymmetrically amplify the polynucleotide strand that has the BsiHKCI sequence towards its 5' terminus. Alternatively, the different restriction endonucleases can be added at different activity levels. Beyond these considerations, preferred nickable restriction endonuclease recognition sites are non-palindromic. A variety of restriction enzymes and their respective recognition sites are disclosed in U.S. Pat. No. 5,270,184 (issued Dec. 14, 1993) at col. 10, lines 29–68, incorporated herein by reference.

A function of the first and second recognition sequences of the amplification primers is to provide templates for generating hemi-modified restriction endonuclease recognition sites. A "hemi-modified restriction endonuclease recognition site" or "hemi-modified recognition site," as used herein, is a double-stranded recognition sequence for a restriction enzyme in which one strand contains at least one modified (or "derivatized") nucleotide which typically prevents cutting of that strand by the restriction enzyme. The other strand of the hemi-modified recognition site, which does not contain a modified nucleotide (or nucleotides) in a position that inhibits cleavage of that strand, is "nicked" by the restriction enzyme. Typical hemi-modified recognition sites are sites involving one or more hemi-phosphorothioated nucleotides in one strand. Suitable restriction enzymes, recognition sites, and modified dNTPs for use in generating a modified recognition site are disclosed in U.S. Pat. No. 5,270,184 (issued Dec. 14, 1993), the disclosure of which is expressly incorporated herein by reference.

A function of the deoxyribonucleoside triphosphates in the process of the present invention is to serve as substrates for the polymerizing enzymes that generate complementary strands of the target nucleic acid sequence using the target as a template, and that generate copies of the target nucleic acid using the complement of the target as a template. Preferred is a set of deoxyribonucleoside triphosphate monomers in which at least one monomer is a modified form of 2'-deoxyguanosine 5'-triphosphate, 2'-deoxyadenosine 5'-triphosphate, 2'-deoxycytidine 5'-triphosphate, or thymidine 5'-triphosphate. Preferably, the modified monomer is 2'-deoxycytidine 5'-O-(1-thiotriphosphate) [i.e., dCTP($\alpha$S)]. In other preferred embodiments, the modified monomer is 2'-deoxyguanosine 5'-O-(1-thiotriphosphate), thymidine-5'-O-(1-thiotriphosphate), 2'-deoxycytidine 5'-O(1-thiotriphosphate), 2'-deoxyuridine 5'-triphosphate, 5-methyldeoxycytidine 5'-triphosphate, or 7-deaza-2'-deoxyguanosine 5'-triphosphate. Those of skill in the art will understand that other modified monomers are within the scope of the invention if they preserve the function of the modified monomer in the methods of the invention. The function of the modified monomer is to contribute to the generation of nickable restriction endonuclease recognition sites. To accomplish this function, the modified monomer must contribute to the inhibition of cleavage of one of the two DNA strands comprising the restriction endonuclease recognition site that is to be nicked. Typically, a modified nucleic acid monomer is incorporated immediately 3' to the cleavage site of the nicking enzyme on one polynucleotide strand, but is not incorporated immediately 3' to the cleavage site on the other strand. The presence of a modified nucleic acid monomer at this position typically inhibits cleavage of that strand. The other strand, lacking a modified nucleotide immediately 3' to the cleavage site of the nicking enzyme, will be cleaved, generating a nick. Other modification schemes that inhibit the cleavage of one strand of a duplex recognition site are also contemplated by the present invention. It is also within the scope of the present invention that more than one nucleic acid monomer is modified. Moreover, skilled artisans will recognize that post-synthesis modification of the appropriate nucleic acid monomer or monomers provides an alternative to the use of a modified nucleic acid monomer.

The present invention employs one or more polymerizing enzymes capable of polymerizing deoxyribonucleoside triphosphates (and modified deoxyribonucleoside triphosphates) into a complementary strand of DNA using an amplification primer and a target nucleic acid sequence as a template. The polynucleotide synthesized in the first extending step will be the complement of a polynucleotide sequence of the target nucleic acid. The polynucleotide synthesized in the second extension step will be the complement of the first extension product and comprise a copy of the target nucleic acid sequence. Sources for the first polymerizing enzyme include eukaryotic, prokaryotic, and viral organisms. The first polymerizing enzymes of the invention may be produced naturally, recombinantly or synthetically, and may constitute holoenzymes, enzyme subunits or fragments thereof. The first polymerizing enzymes also may be treated prior to use in the invention, for example by reducing agents. Preferred as a first polymerizing enzyme in the present invention is an RNA-dependent DNA polymerase when the target nucleic acid is an RNA, or a DNA-dependent DNA polymerase when the target nucleic acid is a DNA. Also preferred is a first polymerizing enzyme effectively lacking a 5'-3' (i.e., 5'→3') exonuclease activity. Another preferred first polymerizing enzyme effectively lacks any exonuclease activity (3'-5' and 5'-3' exonuclease activities). More preferred is a thermostable first polymerizing enzyme capable of sustaining effective catalytic activity at temperatures of 45°–85° C., more preferably 60° C. Use of a thermostable first polymerizing enzyme would permit maximal rates of polynucleotide synthesis at temperatures that would also maximize the fidelity of primer annealing, thereby minimizing the production of undesired polynucleotides. Preferred first polymerizing enzymes include, but are not limited to, reverse transcriptases such as Avian Myeloblastosis Virus Reverse Transcriptase (AMV-RT), Moloney Murine Leukemia Virus Reverse Transcriptase (MMLV-RT), Superscript II (Life Technologies, Inc., Rockville, Md.), and DNA polymerases such as *E. coli* DNA polymerase, *E. coli* DNA polymerase (Klenow fragment), exo⁻ *E. coli* DNA polymerase (Klenow fragment), Bst DNA polymerase, Taq DNA polymerase, Tfl DNA polymerase, and Tth DNA polymerase. It is also within the scope of the present invention that the first polymerizing enzyme have both reverse transcriptase activity and DNA polymerase activity. In such an enzyme, the reverse transcriptase activity copies an RNA target nucleic acid sequence by producing its cDNA, while the DNA polymerase copies DNA target nucleic acids.

A step in the process of the present invention is "separating the target nucleic acid sequence from the first modified polynucleotide extension product." When the target nucleic acid sequence is an RNA sequence and the first modified polynucleotide extension product is a cDNA, one means for separating the target nucleic acid sequence from the first modified polynucleotide extension product is an enzyme activity. Preferably, the enzyme destroys the RNA strand, which contains the target sequence, by partial or complete hydrolysis. For example, an RNA/DNA duplex may be subjected to RNase H activity, effectively yielding a single-stranded cDNA. It is understood in the art that the RNase H activity may be provided by a distinct enzyme such as E. coli RNase H, or an effectively catalytic fragment thereof. The RNase H activity may also be provided by more versatile enzymes exhibiting RNase H activity, such as AMV-RT or MMLV-RT, or catalytically active fragments thereof. As an alternative to enzymatic separation, which is RNA specific, the separating step is also capable of being performed by physical means (e.g., heat) or chemical means (e.g., changes in pH), which are more non-specific, to effectively separate the strands of duplex polynucleotides. The use of enzymatic, physical and chemical means for separating (i.e., rendering single stranded) complementary strands of nucleic acid from one another are well known in the art.

In the second "extending" step of the process of the present invention, a second polymerizing enzyme capable of strand displacement (i.e., separation of a polynucleotide strand hybridized to a "template" strand by primer extension to generate another strand complementary to the "template" and substantially identical to the displaced strand over the region where both complementary strands are able to hybridize to the template) is used. The second polymerizing enzyme catalyzes the synthesis of a polynucleotide complementary to the first extension product, or "template" as used in the preceding parenthetical reference. When the target nucleic acid sequence is an RNA sequence, a second polymerizing enzyme activity (i.e., a DNA polymerase activity) may be needed. As discussed above, a single enzyme may have both reverse transcriptase activity and DNA polymerase activity. Examples of such enzymes are known in the art and include, e.g., AMV-RT and MMLV-RT. A preferred second polymerizing enzyme for use in the second extending step is a DNA-dependent DNA polymerase. Moreover, when the target nucleic acid is a DNA, the first polymerizing enzyme and the second polymerizing enzyme are preferably the same. An example of such a polymerizing enzyme is E. coli DNA polymerase, or a catalytically active subunit or fragment thereof. Preferably, this second polymerizing enzyme lacks exonuclease activity, particularly a 5'-3' exonuclease activity. For example, exo⁻ E. coli DNA polymerase (Klenow fragment), which is commercially available (Molecular Biology Resources, Inc., Milwaukee, Wis.), is a preferred second polymerizing enzyme. It is also within the scope of the present invention that DNA polymerases used in either or both of the extending steps include polymerizing enzymes that are thermostable up to 85° C. Preferred thermostable DNA polymerases include, but are not limited to, Tfl DNA polymerase, Taq DNA polymerase, Tth DNA polymerase, and Bst DNA polymerase.

At the end of the nicking step, i.e., step (f) in Applicants' method for segregating a copy of a target nucleic acid sequence, the Applicants' method provides a double-stranded polynucleotide comprising a segregated copy of the target nucleic acid sequence as a first strand and its complement as a second strand hybridized thereto, the two strands in combination defined at opposing ends by a first and a second nickable recognition site for a first and second restriction endonuclease, respectively.

The above-described method for segregating an amplifiable copy of a target nucleic acid that is found within a single-stranded polynucleotide may conveniently be performed in a single reaction mixture containing all of the reactants mentioned therein. In this latter and preferred embodiment, the above-mentioned hybridizing, extending, and nicking steps occur spontaneously in the reaction mixture with no active process required other than providing the reaction mixture. However, to provide a proper nucleic acid substrate for the first and second spontaneous hybridizing steps of the above-described process, the reaction mixture is subjected to at least one separating step wherein any double-stranded nucleic acid formed in the reaction mixture is separated into single-stranded polynucleotides capable of hybridizing with the appropriate target-seeking primer which is then extended in the 3' direction across the target template.

Accordingly, when the preferred embodiment of the Applicants' method of segregating a copy of a target nucleic acid sequence is expressed in terms of the active steps, it is substantially shorter than Applicants' first described embodiment. Thus, Applicants' preferred embodiment is directed to a method for segregating a copy of a target nucleic acid sequence found within a single-stranded polynucleotide, the segregated copy suitable for use in amplifying the target nucleic acid sequence, the method comprising:

(a) providing a reaction mixture comprising:
(i) a sample containing or suspected of containing a target nucleic acid sequence positioned within a single-stranded polynucleotide at other than an end of the polynucleotide;
(ii) a first polymerizing enzyme capable of polymerizing deoxyribonucleoside triphosphates by extending a hybridized primer, using the single strand of the polynucleotide as a template, and a second polymerizing enzyme capable of polymerizing deoxyribonucleoside triphosphates by extending a hybridized primer and also being capable of strand displacement, with the proviso that when the target nucleic acid is a DNA, the first polymerizing enzyme is optionally the same as the second polymerizing enzyme;
(iii) a mixture of deoxyribonucleoside triphosphates that includes a modified deoxyribonucleoside triphosphate;
(iv) a first amplification primer capable of hybridizing to the target nucleic acid sequence and forming a hybridized primer therewith, the first amplification primer comprising an oligodeoxyribonucleotide having a 3' end and a 5' end, the 3' end of the first amplification primer being complementary to the 3' end of the target nucleic acid sequence, the 5' end of the first amplification primer having a first recognition sequence for a first restriction endonuclease that is capable of nicking one strand of a double-stranded hemi-modified recognition site for the first restriction endonuclease; and
(v) a second amplification primer comprising an oligodeoxyribonucleotide having a 3' end and a 5' end, the 3' end of the second amplification primer being complementary to the 3' end of the complement of the target nucleic acid sequence and capable of hybridizing thereto, the 5' end of the second amplification primer having a second recognition sequence for a second restriction endonuclease that is capable of nicking one strand of a double-stranded hemi-modified recognition site for the second restriction endonuclease;

(b) subjecting the reaction mixture to a means for separating any double-stranded nucleic acid in the reaction mixture into single strands; and (c) allowing the reaction mixture sufficient time for hybridization, primer extension, and nicking to occur, whereby there is produced a double-stranded polynucleotide extension product suitable for amplification comprising a segregated copy of the target nucleic acid sequence and a segregated copy of the complement of the target nucleic acid sequence, the double-stranded polynucleotide extension product being defined at opposing ends by a first nickable restriction site and a second nickable restriction site for the first and second restriction endonucleases, respectively.

The above-described method is referred to herein as "the short segregation method, steps (a)–(c)." In step (a) of the above method, the reaction mixture is provided in an aqueous or substantially aqueous medium suitable for nucleic acid polymerization. The use of such media is well known in the art. Step (b) of the short segregation method, steps (a)–(c), utilizes a means for separating any double-stranded nucleic acid into single strands such that the strands would act as templates for further hybridization and extension reactions involved in segregating a copy of the target nucleic acid sequence from the larger polynucleotide in which it was originally found. The means for separating double-stranded nucleic acid into its two component single strands are well known in the art and encompass the inclusion or addition of an RNase, e.g., RNase H, into the reaction mixture when a cDNA-RNA duplex is formed in step (a), and the target nucleic acid is within a segment of RNA. It is also within the scope of the present invention that the polymerizing enzyme also have RNase-like activity. Other less specific means for separating, described above in detail, include the use of chemical means, such as pH, or physical means such as the application of heat. All of these techniques are well known in the art and need no further description herein.

Step (b) of "the short segregation method, steps (a)–(c)" is typically performed on one occasion when the target nucleic acid is an RNA, such as found in an RNA duplex or an RNA-DNA duplex, or when target nucleic acid is provided as a single-stranded DNA or RNA. This same step (b) is typically performed on two occasions when the target nucleic acid is DNA and it is provided in the sample as a DNA duplex or as an RNA-DNA duplex.

Because the amplifiable copy of the target nucleic acid sequence and its complement are each positioned between recognition sequences for a first and second restriction enzyme, the segregated copy of the target nucleic acid sequence, unlike the original target nucleic acid sequence, is isolated from the non-target nucleic acid sequences in the polynucleotide fragment. Thus, the segregated copy of the target nucleic acid sequence and its complement are capable of being amplified exponentially under substantially isostatic conditions.

Therefore, in its second aspect, the present invention is directed to a method for amplification of a target nucleic acid sequence that utilizes the segregated copy of the target nucleic acid sequence, as obtained above, as an intermediate, i.e., as an amplification template, in a polynucleotide amplification reaction scheme. Accordingly, the second aspect of the present invention is directed to a method for amplifying a target nucleic acid sequence within a mixture of polynucleotides, the method comprising steps (a)–(f) above and further including the steps of:

(g) amplifying the segregated copy of the target nucleic acid sequence and its complement by contacting the third double-stranded polynucleotide with the first restriction endonuclease and the second restriction endonuclease in the presence of a mixture of an enzyme having a DNA polymerase activity that is capable of strand displacement, deoxyribonucleoside triphosphates, and a modified deoxyribonucleoside triphosphate, whereby the first and second recognition sequences of the first and the second recognition sites are nicked and the 3' ends of the sites that are nicked are extended, generating a nascent target nucleic acid sequence or its complement, and displacing the downstream copy of the target nucleic acid sequence or its complement in the process; and (h) allowing step (g) to continue for a sufficient time to produce a detectable amount of the segregated copies of the target nucleic acid sequence.

The amplifying step of the method according to the invention creates at least one nick, i.e., cleavage of one strand of a duplex polynucleotide at a defined position. In addition to a lone single-stranded cleavage, the invention contemplates the contemporaneous cleavage, by two independent nicking events, of both strands of a duplex polynucleotide. However, such contemporaneous cleavage events cannot occur on the same side of the target sequence. The cleavage of each strand must be offset, essentially bracketing the target nucleic acid sequence between the cleavage positions. A preferred nicking activity is supplied by the combination of a substantially hemi-modified restriction endonuclease recognition site and the cognate restriction endonuclease. Restriction endonucleases capable of nicking hemi-modified recognition sites include, but are not limited to, AccI, AlwI, AvaI, BsaI, BsiHKCI, BsmI, BsoBI, BsrI, BstXI, DpnI, Fnu4HI, FokI, HincII, HindII, HphI, MspI, NciI, NlaIV, NspI, PflMI, and Tth111I. Particularly preferred for nicking are BsiHKCI and its recognition site, wherein the site is hemi-modified by incorporation of dCTP ($\alpha$S). Skilled artisans will recognize other means for nicking the duplex polynucleotides of the invention. For example, replication enzymes can cleave a single strand of duplex polynucleotide. Alternatively, primers specifying a single strand of a DpnI recognition site can be methylated using dam Methylase. Amplicon (i.e., segregated, and amplified, copies of the target nucleic acid sequence flanked by nickable sites) is then produced with unmodified nucleic acid monomers and DpnI as the nicking enzyme, because the enzyme only cleaves methylated DNA strands.

Further, any restriction endonuclease modification that alters restriction enzyme activity to preferentially nick one of the two nucleic acid strands of a recognition site would function in this invention. For example, a type IIS restriction endonuclease such as FokI can be re-engineered by site-directed mutagenesis to inactivate one of its two cleavage centers, such that the re-engineered enzyme cleaves only one of its substrate's two cleavage sites, thereby becoming a nicking enzyme in accordance with the invention.

The amount of time that the amplifying step is allowed to proceed is dependent upon the activity of the polymerizing enzyme and the temperature, because saturating amounts of deoxyribonucleoside triphosphates and a modified deoxyribonucleoside triphosphate are used. A typical amplification time is approximately 60 minutes.

Alternatively, the method of amplifying a target nucleic acid sequence that is located within a single-stranded polynucleotide is performed by taking steps (g) and (h) as described above and adding them as steps (d) and (e), respectively, to the short segregation method, steps (a)–(c), with one modification to the language of each one of steps (g) and (h). First, the step (g) reference to "contacting the third double-stranded polynucleotide" is replaced in step (d) by "contacting the double-stranded polynucleotide extension product." Second, the step (h) reference to "step (g)" is replaced in step (e) by a reference to "step (d)." The method of amplification of this paragraph is referred to hereinafter as "the short amplification method, steps (a)–(e)."

A third aspect of the invention is directed to a method for determining the presence of a target nucleic acid sequence. In particular, the invention comprehends a method for determining the presence of a target nucleic acid sequence within a single-stranded polynucleotide comprising steps (a)–(h), as discussed above, and further including the step of:

(i) determining the presence of a detectable amount of the segregated copies of the target nucleic acid sequence whereby the presence of a detectable amount of the target nucleic acid sequence indicates the presence in the sample of the genotype or organism associated with the target nucleic acid sequence.

In a preferred embodiment, the method of the present invention is used to determine the pathogenic presence of *Cryptosporidium parvum* in a sample suspected of containing *C. parvum*. The pathogenic presence of *C. parvum* is determined by subjecting the sample to the method of steps (a)–(i) of the present invention. Two amplification primers, P1 and P2, are used to detect the presence of *C. parvum* nucleic acids by amplifying a portion of the *C. parvum* 18S rRNA gene. The nucleotide sequence of P1 is presented in SEQ ID NO:2; the P2 nucleotide sequence is presented in SEQ ID NO:3. Any one or more of a variety of conventional techniques for DNA detection are employed to detect the amplified target nucleic acid sequence, including visualization of stained gels containing electrophoretically fractionated reaction products. Alternatively, a probe-extension assay involving a radiolabel-based detection system may be used (see below). Such detection techniques are conventional and well known in the art.

In another preferred embodiment, the susceptibility to human breast cancer is determined. In particular, a sample containing genomic DNA from a female, or male (i.e., carrier), patient is used as a source of a target nucleic acid sequence. Primers are designed to anneal to genomic DNA sequences bracketing mutational sites diagnostic for genetic alleles implicated in a higher genetic incidence of breast and ovarian cancer. In particular, mutations in the BRCA1 gene on chromosome 17q21.1 are associated with dominant high-penetrance breast and ovarian cancer susceptibility. Women who are heterozygous for such mutations have an 85% risk of breast cancer and a 63% risk of ovarian cancer during their lives. See Boyd et al. "A Human BRCA1 Gene Knockout," *Nature* 375:541–542 (1995) which is incorporated herein in its entirety by reference. The BRCA1 gene was mapped in 1990 and has 24 exons that encode a protein of 1863 amino acids. See Hall et al., *Science* 250:1684–1689 (1990) which is incorporated herein by reference. The BRCA1 gene has also been isolated. See Simard et al., *Nature Genet.* 8:392–398 (1994) and Miki et al., *Science* 266:66–71 (1994) both of which are incorporated herein by reference. BRCA1 germline mutations have been identified in more than 80 families wherein these cancers are prevalent. See Futreal et al., *Science* 266:120–122 (1994), Castallia et al., *Nature Genet.* 8:387–391 (1994), Friedman et al., *Nature Genet.* 8:399–404 (1994), and Schattuck-Eidens et al., *A.J. Med. Ass.* 273:535–541 (1993) each of which is incorporated herein by reference. Boyd et al. (1995) reports finding a deletion of two "A" nucleotides at position 2,800 in the BRCA1 sequence ($AA_{2800}$) i.e., in exon 11, which results in a stop codon at nucleotide 2,820, in a family having a high incidence of breast and/or ovarian cancer. This is the same $AA_{2800}$ mutation reported by Friedman et al. (1994). The method of amplification of the present invention can be used to either amplify known mutations, such as those described above, whereupon the mutant amplicon is detected and its presence is associated with an increased risk for breast and/or ovarian cancer in females carrying the mutation. For example, using the known sequence of BRCA1 and the sequence associated with the deletion ($AA_{2800}$), a first amplification primer is constructed such that the terminal two bases at its 3' end are complementary to the two bases upstream from the two-base deletion ($AA_{2800}$). Using the known sequence for exon 11 of BRCA1, a second amplification primer is constructed to hybridize to the downstream complement. The first amplification primer of the above-described construct is capable of fully hybridizing only with the mutation ($AA_{2800}$). In BRCA1 alleles lacking this mutation, the 3' terminus of the first amplification primer does not hybridize and an amplification product is not produced. Conversely, in BRCA1 genes having this mutation, the mutation is amplified to a detectable amount.

In an alternative embodiment, the method of the present invention is used as a screening technique for detecting mutations in any or all of the 24 exons of the BRCA1 gene. For example, relying upon the published sequence of the BRCA1 gene, a first amplification primer is designed so that its 3' end binds to the 3' end of a target exon of interest (or to the intron 3' thereto). A second amplification primer in accordance with the present invention has a 3' end designed to bind to the 3' end of the complement of the target exon of interest (or to the complement of an intron 3' thereto). The 5' end of each of the first and second amplification primers are associated with recognition sequences for restriction enzymes capable of nicking a hemi-modified recognition, or restriction, site. See e.g., U.S. Pat. No. 5,270,184 at col. 10 for recognition sequences and restriction enzymes capable of generating a hemi-modified restriction site. The primers are designed to bracket the target exon of interest of the known BRCA1 gene. See also Nowak, *Science* 268:1700–1701 (1995), which is incorporated herein by reference. The amplified exon (i.e., target nucleic acid sequence) can be separated electrophoretically using techniques known in the art, such as single-strand conformational polymorphism (SSCP), to look for mutations within a locus associated with an increased incidence of breast cancer.

In another embodiment, amplification primers bracket regions of the ATM gene known to be informative in diagnosing ataxia telangiectasia, a hereditary disease. Savitsky et al., *Science* 268:1749–1753 (1995), which is incorporated herein by reference, reports the mapping and partial cDNA sequence of the single gene responsible for the disease. The amplicon produced using the method of the present invention is amenable to the rapid determination of a partial human genotype using techniques that are standard in the art. Knowledge of the relevant partial human genotype, in turn, facilitates the determination of a particular mammalian condition such as the propensity to develop a particular disease trait. That knowledge provides guidance for treatment efforts, including prophylactic treatments (i.e., genetic counseling).

In another embodiment, the method of detecting a target nucleic acid sequence in accordance with the present invention is used to detect the presence of a retrovirus such as HIV-1, by amplifying the known nucleic acid sequences in the HIV-1 genome encoding such structural proteins as reverse transcriptase (RT), HIV-1 protease, or integrase, the regulatory proteins (Tat, REV, Nef), or the virion structural and accessory proteins (Env, Gag, Vif, Vpr, Vpu). In particular, using the known sequence of HIV-1 RT, a pair of amplification primers are made in accordance with the present invention, the first having a 3' end that hybridizes to the 3' end of a target nucleic acid sequence encoding at least part of the RT (either as RNA or its cDNA), and the second amplification primer having a 3' end that hybridizes to the 3' end of the complement of the target sequence. Because the two amplification primers of the present method bracket the target nucleic acid sequence, needing no more than approximately 16 complementary bases per primer, the present method would function even where partial sequences at opposing ends of a target nucleic acid sequence of interest are known. In the present embodiment, the amplification primers each have recognition sequences at their 5' ends for a restriction endonuclease that is capable of nicking a hemi-modified recognition site. Employing the above-described amplification primers with nucleic acid from a sample suspected of containing HIV-1, in the presence of a mixture of deoxyribonucleoside triphosphates and a modified deoxyribonucleoside triphosphate as described in steps (a)–(i) above, the method of the present invention will amplify and allow for detection of any HIV-1 RT in the sample. The above method of detection of the present invention is amenable to the amplification of target nucleic acid sequences of HIV-1, such as RT, which rapidly undergo mutation, as revealed by drug therapy with anti-RT agents such as AZT, DDC, DDI, 3TC, and the like, all of which act as chain terminators during DNA synthesis.

In an alternative embodiment, the method of determining the presence of the target nucleic acid sequence comprises taking step (i) as described above and adding it as step (f) to the short amplification method, steps (a)–(e). This method of determining the presence of a detectable amount of target nucleic acid sequence is referred to hereinafter as "the short determining method, steps (a)–(f)."

Another aspect of the invention is directed to a kit including components for practicing the method of the invention, comprising:

(a) a polymerizing enzyme capable of polymerizing deoxyribonucleoside triphosphates to generate a first product consisting essentially of a complement of a template, the enzyme being capable of strand displacement;

(b) a pair of amplification primers comprising a first amplification primer and a second amplification primer, the first amplification primer having a 3' end that is complementary to the 3' end of a target nucleic acid sequence that is positioned within a larger polynucleotide at a location other than a terminus, and a 5' end that includes a first recognition sequence for a first restriction endonuclease capable of nicking a hemi-modified first recognition site, the second amplification primer having a 3' end that is complementary to the 3' end of the complement of the target nucleic acid sequence and a 5' end that includes a second recognition sequence for a second restriction endonuclease capable of nicking a hemi-modified second recognition site;

(c) from one to two restriction endonucleases capable of nicking a substantially hemi-modified restriction endonuclease recognition site;

(d) deoxyribonucleoside triphosphates; and (e) a modified deoxyribonucleoside triphosphate.

It is within the scope of the present invention that the first recognition sequence and the second recognition sequence may be the same or different. In addition, the above-described kit may further include an RNA-dependent DNA polymerase. Further, it is also within the scope of the present invention that the kit further include buffers and ions sufficient to maintain effective activity of the enzymes included therein. In the kit of the present invention, the enzymes are provided in a lyophilized state or in a stabilizing solution.

In a preferred embodiment, enzymes are provided in a buffered solution stabilized with glycerol and maintained at $-20°$ C. Provided in the kit are AMV Reverse Transcriptase, RNase H, Bst DNA polymerase, BsiHKCI and an enzyme dilution buffer containing bovine serum albumin, $MgCl_2$, additional salts, maltitol and trehalose. Those of skill in the art will recognize that other enzymes, enzyme subunits, and fragments thereof may be used in the kit according to the invention. The deoxyribonucleoside triphosphates that are provided in the kit of the present invention include three of the four members of the group consisting of 2'-deoxyguanosine 5'-triphosphate, 2'-deoxyadenosine 5'-triphosphate, thymidine 5'-triphosphate, and 2'-deoxycytidine 5'-triphosphate, with the proviso that the deoxyribonucleoside triphosphate that is not included in the kit is present in one of its modified forms. Modified deoxyribonucleoside triphosphates for use in the present invention have been described herein. Preferred modified deoxyribonucleoside triphosphates are 2'-deoxyguanosine 5'-O-(1-thiotriphosphate), 2'-deoxyadenosine 5'-O-(1-thiotriphosphate), thymidine 5'-O-(1-thiotriphosphate) and 2'-deoxycytidine 5'-O-(1-thiotriphosphate). In other preferred embodiments, tetramethylammonium chloride or tetraethylammonium chloride may be added to the reaction components.

In a preferred kit according to the invention, the following components are provided in standard 1.4 ml screw-capped and gasketed microcentrifuge tubes. A 10×buffer stock contains 0.5 ml of a solution consisting of 350 mM $K.PO_4$ (pH 7.6). In a second tube, a 10X stock of additional reagents contains 0.5 ml of a solution containing 102 mM $MgCl_2$, 7.0 mM Tris-HCl (pH 7.9), 34 mM KCl, 7.0 mM dithiothreitol, 20% (w/v) maltitol, and 13.4% (w/v) trehalose. Deoxyribonucleoside triphosphates are provided in a third tube containing 0.5 ml of a 10×stock solution consisting of 5 mM dGTP, 5 mM dATP, 5 mM TTP, and 14 mM dCTP($\alpha$S). Proteins are provided in a fourth tube containing 0.5 ml of a 10×stock solution consisting of 800 units of AMV Reverse Transcriptase, 24 units of *E. coli* RNase H, 800 units of Bst DNA polymerase, 15,000 units of BsiHKCI, and 7.0 mg/ml bovine serum albumin in a stabilized glycerol solution maintained at $-20°$ C. As formulated, the kit provides reagents sufficient for 100 conventional amplification reactions. The kit user supplies the sample containing or suspected of containing the target nucleic acid sequence. Each of the two primers (e.g., SEQ ID NOs. 2 and 3; 0.5 $\mu$M) exhibits a target binding site of at least about 16 bases towards the 3' terminus of each primer. Towards the 5' terminus of each of the two primers, a sequence specifying one strand of the recognition site for BsiHKCI, 5'-CTCGGG-3' (i.e., a recognition sequence), is provided. In use, for a heat denaturation step in a method according to the invention, the buffer is combined with the deoxyribonucleoside triphosphates, sample nucleic acid, and primers. For example, a denaturation step involving incubation at 100° C. for 2 min. is used. Following an incubation at a suitable annealing temperature, for example 2 minutes at about 60° C., the remaining components are added and the reaction is allowed to proceed, for example at about 60° C. for 60 minutes.

Segregation and/or Amplification Scheme

Figure 1B:
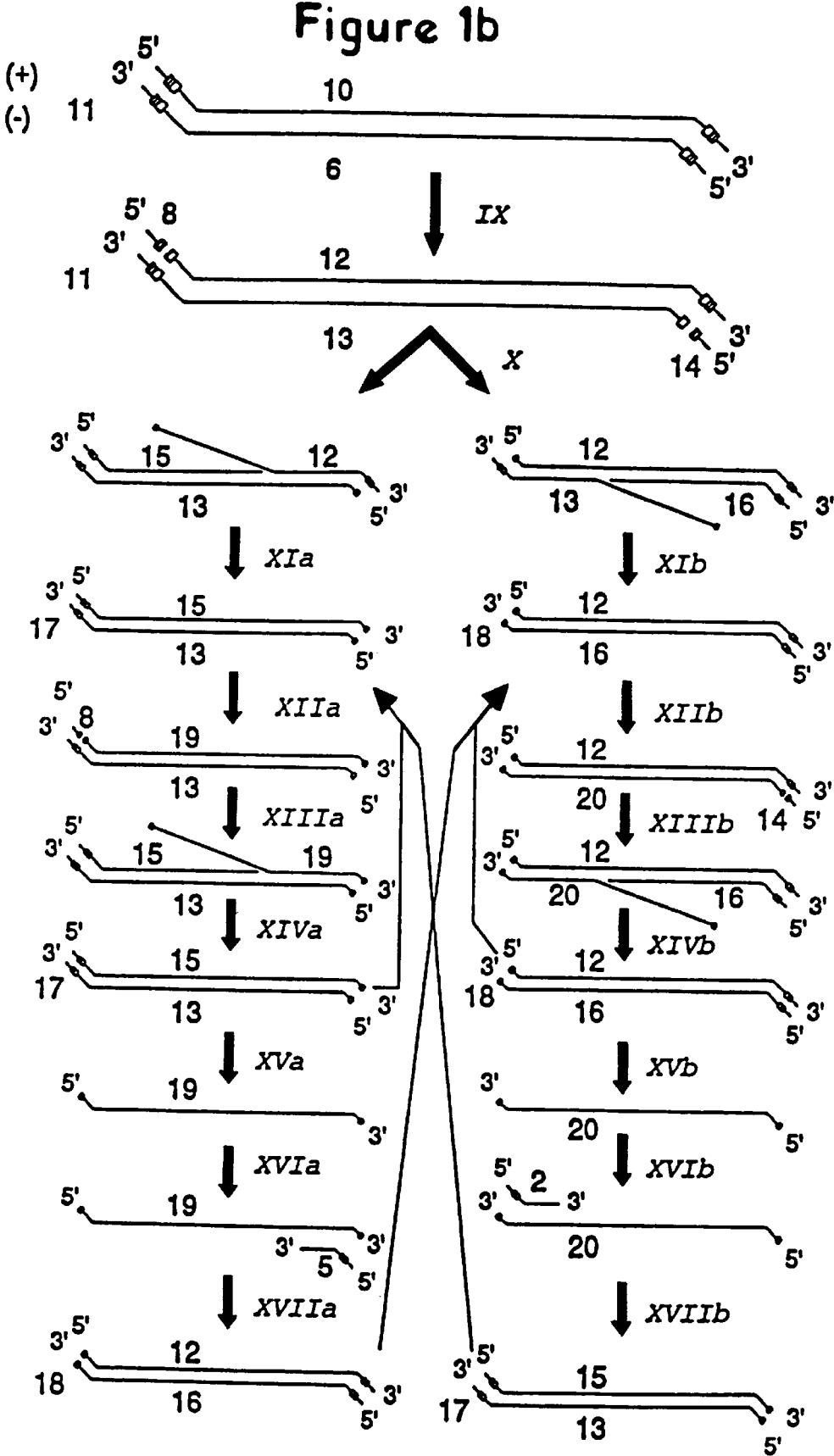

The segregation/amplification scheme implemented by the method of the present invention is shown in FIGS. 1a and 1b. For purposes of illustration, an embodiment involving a target nucleic acid sequence in a single-stranded polynucleotide 1 is exemplified (FIG. 1a). Initially, sequence data deduced from the target nucleic acid sequence (e.g., RNA or DNA) is used to design two primers, (+) primer 2 and (−) primer 5. Each primer contains, towards its 5' end, a restriction endonuclease recognition sequence for a restriction endonuclease which nicks the double-stranded, hemi-modified DNA produced during segregation and amplification. The 3' end of (+) primer 2 contains a target binding region exhibiting a sequence complementary to the 3' end of the target nucleic acid sequence within the polynucleotide 1. The 3' end of (−) primer 5 contains a target binding region exhibiting a sequence which is complementary to the 3' end of the complement of the target nucleic acid sequence within the polynucleotide 1, a sequence that is found in a complementary (+) strand 3. The complement of the target binding region of (+) primer 2 and the target binding region of (−) primer 5 in the polynucleotide 1 delimit the target nucleic acid sequence because it is the polynucleotide portion between the two primers, as well as the primer sequences themselves, that will be segregated and amplified.

The amplification scheme begins with a separating step (not shown), for example by polynucleotide denaturation, if the target nucleic acid sequence is in a double-stranded form. Denaturation can be accomplished by, for example, the application of heat or a change in pH using techniques standard in the art. In a preferred embodiment, strand separation is accomplished by heating a reaction containing the polynucleotide 1 in the presence of the two primers, (+) primer 2 and (−) primer 5, and a mixture comprised of deoxyribonucleoside triphosphates (at least one of which is modified), buffer, and salts. In particular, separation is accomplished by raising the temperature of the reaction to 65–100° C. for several minutes. Particularly preferred is separation by incubation at 100° C. for two minutes. The temperature is lowered to an appropriate temperature, for example 60° C., to allow (+) primer 2 to anneal to the polynucleotide 1, suspected of containing the target polynucleotide (step I in FIG. 1a, not shown).

In step II in FIG. 1a and wherein the polynucleotide 1 is an RNA molecule, a polymerizing enzyme capable of template-directed nucleic acid polymerization, for example an RNA-dependent DNA polymerase such as a reverse transcriptase, synthesizes a complementary (+) strand 3 by extension of a first amplification primer, (+) primer 2, using the polynucleotide 1 as a template. When the polynucleotide 1 is RNA, reverse transcriptase is a preferred enzyme for catalyzing the synthesis of a complementary (+) strand 3, which, in this case, is a cDNA. The reaction is performed in the presence of deoxyribonucleoside triphosphates and at least one modified deoxyribonucleoside triphosphate. Extension of (+) primer 2 by a polymerizing enzyme such as a DNA polymerase or a reverse transcriptase forms complementary (+) strand 3. The hybridization of complementary (+) strand 3 to polynucleotide 1 yields product 4, a partially duplex (i.e., partially double-stranded) polynucleotide. The complementary (+) strand 3 is separated from the polynucleotide 1 by methods well known in the art. When the polynucleotide 1 is an RNA molecule, separation is preferably achieved using an enzyme which selectively degrades the RNA polynucleotide 1 participating in an RNA/DNA duplex, illustrated by the dashed line depicting partially degraded polynucleotide 1' in step III of FIG. 1a. Suitable enzymes are those which selectively act on the RNA strand of an RNA/DNA duplex and include enzymes which comprise an RNase H activity. This step may be catalyzed by a reverse transcriptase which contains RNase H activity or by a separate RNase H enzyme. A preferred enzyme is *E. coli* RNase H. Other preferred methods to effect strand separation include the application of heat or alteration of the pH of the mixture. Whether proceeding through a stage involving a partially degraded polynucleotide 1' or not, eventually the complementary (+) strand 3 is rendered functionally single stranded as illustrated by step IV.

In step V, the complementary (+) strand 3 is contacted with a second amplification primer, (−) primer 5. The (−) primer 5 anneals to the region of complementary (+) strand 3 that contains sequence complementary to the sequence defining one end of the target nucleic acid sequence, a sequence that is essentially the same as the sequence of the 3' binding region of (−) primer 5. As defined herein, sequences which differ primarily in the substitution of uracil for thymine and ribose for deoxyribose, that is RNA and DNA sequences of essentially the same informational content, are essentially the same sequences and constitute copies of one another.

In step VI, (−) primer 5 is extended using complementary (+) strand 3 as a template, and deoxyribonucleoside triphosphates, wherein at least one of the deoxyribonucleoside triphosphates is modified. This extension reaction generates a modified (−) strand 6 participating, with complementary (+) strand 3, in a partial duplex polynucleotide 7 (step VI).

Partial duplex polynucleotide 7 contains two incompletely modified polynucleotide strands. The 5' terminus of each strand, modified (−) strand 6 and complementary (+) strand 3, is provided by an unmodified primer sequence, including an unmodified restriction endonuclease recognition sequence. The 5' end of (−) strand 6 is contributed by (−) primer 5; the 5' end of complementary (+) strand 3 is contributed by (+) primer 2. Consequently, the single engineered restriction endonuclease recognition site in the partial duplex polynucleotide 7 is a substantially hemi-modified recognition site because of the participation of unmodified (+) primer 2 in forming that site. In FIGS. 1a and 1b, nickable restriction endonuclease recognition sites are illustrated by juxtaposed boxes of different patterns. The boundary between adjacent boxes represents the cleavage site.

In step VII, the hemi-modified restriction endonuclease recognition site in the partial duplex polynucleotide 7 is nicked by restriction endonuclease (e.g., BsiHKCI) cleavage of the single-stranded unmodified restriction endonuclease sequence. The nick produces an upstream (+) strand 8 and a downstream (+) strand 9, both annealed to the modified (−) strand 6 which is not nicked. The upstream (+) strand 8 has a free 3' terminus available to prime the synthesis of another polynucleotide strand complementary to modified (−) strand 6.

In step VIII, the 3' end of upstream (+) strand 8 is extended to form a modified (+) strand 10 complementary to modified (−) strand 6. This step displaces (+) strand 9 in the process. The annealing of modified (+) strand 10 to (−) strand 6 yields a double-stranded polynucleotide fragment 11 that is substantially free of non-target DNA. The non-target DNA in double-stranded polynucleotide fragment 11 is primarily the two introduced restriction endonuclease recognition sites. Therefore, double-stranded polynucleotide fragment 11 is a double-stranded form of a segregated copy of the target nucleic acid sequence suitable for amplification in the method of the present invention. Double-stranded polynucleotide fragment 11 contains two substantially hemi-modified, and nickable, restriction endonuclease recognition sites, one located at each end of the fragment. The two nickable restriction endonuclease recognition sites in double-stranded polynucleotide fragmemt 11 may be the same or different.

In FIG. 1b, the double-stranded polynucleotide fragment 11 cycles through a process of nicking at the hemi-modified restriction endonuclease recognition sites (step IX) and extensions of the 3' termini produced by the nicks, resulting in strand displacements of the downstream strands containing the target nucleic acid sequence or its complement (step X). More specifically, nascent (+) strand 15 is formed by extending upstream (+) strand 8. The synthesis of nascent (+) strand 15 displaces the pre-existing displaced (+) strand 12. Although not shown in FIG. 1b, displaced (+) strand 12 binds (−) primer 5. Extension of (−) primer 5 yields nascent (−) strand 16 (not shown). As synthesized, nascent (+) strand 15 is hybridized to displaced (−) strand 13, forming nascent duplex 17 as shown in step XIa. Nascent duplex 17 contains one regenerated nickable restriction endonuclease recognition site. Nicking that site cleaves nascent (+) strand 15, forming upstream (+) strand 8 and minimal downstream (+) strand 19 (step XIIa). In step XIIIa, extension of upstream (+) strand 8 generates another copy of nascent (+) strand 15 while displacing minimal downstream (+) strand 19. In step XIVa, the extension reaction is completed, yielding a complete copy of nascent (+) strand 15 hybridized to displaced (−) strand 13, thereby regenerating nascent duplex 17. Nascent duplex 17 recycles through steps XIIa, XIIIa, and XIVa. The displaced minimal downstream (+) strand 19 (step XVa) hybridizes to (−) primer 5 (step XVIa). Extension of (−) primer 5 produces a copy of nascent (−) strand 16; extension of minimal downstream (+) strand 19 using the sequence of (−) primer 5 as a template yields a copy of displaced (+) strand 12 (step XVIIa). As synthesized, displaced (+) strand 12 is hybridized to nascent (−) strand 16, thereby creating a copy of nascent duplex 18 which serves as a substrate in step XIIb. The preceding discussion traced the fate of upstream (+) strand 8 and displaced (+) strand 12 from step X. An analogous series of reactions is involved in manipulations directed to upstream (−) strand 14 and displaced (−) strand 13 (step X).

In step XIb, extension of upstream (−) strand 14 generates a copy of nascent (−) strand 16 and displaces the previously annealed displaced (−) strand 13. Displaced (−) strand 13 hybridizes to (+) primer 2; extension of (+) primer 2 yields nascent (+) strand 15 which, hybridized to displaced (−) strand 13, generates a copy of nascent duplex 17 (not shown). In step XIIb, nascent (−) strand 16, participating in nascent duplex 18, is nicked, thereby creating upstream (−) strand 14 and minimal downstream (−) strand 20. Extension of upstream (−) strand 14 generates nascent (−) strand 16 and displaces minimal downstream (−) strand 20 (step XIIIb). In step XIVb, the synthesis of a copy of nascent (−) strand 16 is complete and, because that strand is hybridized to displaced (+) strand 12, a copy of nascent duplex 18 is created. Nascent duplex 18 then cycles back through steps XIIb, XIIIb, and XIVb. The displaced minimal downstream (−) strand 20 (step XVb) hybridizes to (+) primer 2 (step XIb). Extension of (+) primer 2 yields a copy of nascent (+) strand 15, and the extension of minimal downstream (−) strand 20 using (+) primer 2 as a template produces displaced (−) strand 13 (step XVIIb). Because nascent (+) strand 15 is hybridized to displaced (−) strand 13, a copy of nascent duplex 17 is generated, which feeds into step XIIa. These steps are repeated during the amplification process.

The (+) primer 2 and (−) primer 5 used in the methods generally have lengths of about 40 nucleotides each. The (+) primer 2 and (−) primer 5 target binding sites should exhibit sequences of such complementarity that they will bind to a target template under the high stringency hybridization conditions presented by standard reaction conditions.

Experimental Section
1. Amplification of an RNA Target Polynucleotide

All chemicals were reagent grade. Moloney Murine Leukemia Virus Reverse Transcriptase and Superscript II Transcriptase were purchased from Life Technologies, Inc. (Rockville, Md.). T3 RNA polymerase came with the Ambion Maxiscript Kit, Ambion, Inc. (Austin, Tex.). All other enzymes were from Molecular Biology Resources, Inc. (Milwaukee, Wis.). Polynucleotides were synthesized and gel purified by Synthetic Genetics (San Diego, Calif.).

RNA templates were prepared using the Ambion Maxiscript Kit according to the manufacturer's recommendations. Briefly, RNA template was prepared by transcription of approximately 2 $\mu$g of plasmid pCPV4.7. Plasmid pCPV4.7 contains the 18S rRNA gene from *Cryptosporidium parvum*. (The plasmid was kindly provided by Norman Pieniazek, Center for Disease Control, Atlanta, Ga.) This plasmid contains a T3 RNA polymerase promoter adjacent to the 18S rRNA gene, with the promoter properly oriented to express that gene. The plasmid was linearized by restriction endonuclease digestion with PvuII and transcribed in vitro using T3 RNA polymerase and an Ambion Maxiscript Kit. The reaction products were treated twice with RNase-free DNase I to ensure complete removal of DNA. The transcript was quantified by comparison to known standards on an agarose gel. The yield was 1.5 $\mu$g of pure transcript.

The final concentrations of components in the reaction were generally 35 mM potassium phosphate (pH 7.6), 1.4 mM dCTP($\alpha$S), 0.5 mM dATP, 0.5 mM dGTP, 0.5 mM TTP, 0.7 mg/ml bovine serum albumin, 10.2 mM $MgCl_2$, 0.7 mM Tris-HCl (pH 7.9), 3.4 mM KCl, 0.7 mM dithiothreitol, 2% maltitol, 1.34% trehalose, 4–8 units AMV Reverse Transcriptase, 0.12–0.24 units *E. coli* RNase H, 8 units Bst DNA polymerase, 150 units of BsiHKCI, and varying amounts of RNA template, as described below for each experiment, in a final reaction volume of 50 $\mu$l. The samples also contained primers P1 and P2 (see below), each present at 0.5 $\mu$M. In addition, the reaction components optionally include tetramethylammonium chloride or tetraethylammonium chloride at between 1–100 mM.

The nucleotide sequence of P1, 5'-ACCCCATCCAATGCATGTc/tcgggTCGTAGTCTTAACCAT-3', is presented in SEQ ID NO:2. [Primer P1 corresponds to (+) primer 2 in FIGS. 1a and 1b]. The nucleotide sequence of P2, 5'-CGATTCGGCTCCAGACTTc/tcgggTGCTGAAGGAGTAAGG-3', is presented in SEQ ID NO:3. [Primer P2 corresponds to (−) primer 5 in FIGS. 1a and 1b]. In the sequences of P1 and P2 shown above, the sequence corresponding to the restriction endonuclease recognition sequence for BsiHKCI is presented in lower case letters, with slashes identifying the restriction endonuclease cleavage, or potential nicking, sites. The sequences 3' to each restriction endonuclease recognition sequence are the target binding regions of P1 and P2.

A 40 $\mu$l sample containing the phosphate buffer, nucleotides, primers, and template was assembled using concentrated reagents. The sample was heated to 100° C. for 2 minutes to denature the template. The sample was then cooled to 50° C. for 2 minutes prior to adding an enzyme mix containing the remaining reaction components, bovine serum albumin, $MgCl_2$, Tris-HCl (pH 7.9), KCl, dithiothreitol, maltitol, trehalose, reverse transcriptase, Bst DNA polymerase, BsiHKCI, and RNase H. In a single-step protocol the sample was incubated for 60 minutes at 50° C., while in a two-step protocol the sample was first incubated at 37° C. for 30 minutes followed by 30 minutes at 50° C.

Amplicon was detected by a probe-extension assay described by Walker et al., Nucl. Acids Res. 20(7):1691–1696 (1992), incorporated herein by reference. Initially, a *Cryptosporidium parvum* detection probe, 5'-AGAGATTGGAGGTTG-3' and presented in SEQ ID NO:4, was radiolabeled as follows. Ten picomoles of the C. *parvum* detection probe, 35 $\mu$Ci of [$\gamma^{32}$P]ATP (6000 Ci/mmol, NEN Research Products, Boston, Mass.), 30 units of polynucleotide kinase, 50 mM Tris-HCl, pH 7.2, 1 mM $MgCl_2$, 5 mM dithiothreitol, 0.1 mM spermidine-HCl in a total volume of 10 $\mu$l were incubated for 30 minutes at 37° C. The reaction was stopped by heating for 5 minutes at 100° C. The radiolabeled C. *parvum* detection probe was then added to five $\mu$l of a solution containing 10 mM each of dATP, dCTP dGTP, and TTP; 5 $\mu$l of 350 mM potassium phosphate, pH 7.6; 1.5 $\mu$l of 200 mM $MgCl_2$; and water to a final total reaction mixture volume of 50 $\mu$l. The radiolabeled detection probe was then used in a detection assay.

Five $\mu$l of the reaction mixture containing the radiolabeled detection probe was combined with 5 $\mu$l of the amplicon mixture and heated to 95° C. for 2 minutes followed by incubation at 37° C. for 2 minutes. At this time, 1 $\mu$l of exo$^-$ DNA polymerase (Klenow fragment; 10 units/$\mu$l) was added to initiate the extension reaction. The sample was incubated for 15 minutes at 37° C. and the reaction was stopped with 11 $\mu$l of a solution containing 95% formamide, 10 mM EDTA, 1 mM dithiothreitol, 0.05% (w/v) bromophenol blue, and 0.05% (w/v) xylene cyanole. Samples were then incubated at 95° C. for 2 minutes and analyzed by electrophoresis on a 10% denaturing polyacrylamide gel. Gels were subsequently subjected to autoradiographic detection techniques standard in the art. In this embodiment of the method according to the invention, the detection procedure yielded products of 57 (full length) and 38 (nicked) nucleotides.

2. Amplification of an RNA Target Polynucleotide Using Various Polymerizing Agents A variety of polymerizing agents were used to amplify an RNA target nucleic acid sequence of the invention. The results are presented in FIG. 2. Reactions were prepared generally as described above in subsection 1.

RNA transcripts for use as templates in the methods of the invention were prepared as described using linearized plasmid pCPV4.7 and T3 RNA polymerase. Each sample of RNA template, capable of supporting a plurality of reactions, contained approximately $10^7$ molecules. RNA transcript copy number was determined by spectrophotometric analysis at 260 nm using concentrated stocks of the template and a transcript size of 1750 bases. Some aliquots of the template were treated with 25 $\mu$g of RNase A in 10 mM Tris-HCl, pH 8.5, 50 mM KCl, in a total volume of 250 $\mu$l for 60 minutes at 37° C. RNA template samples were used without further treatment.

Amplification reactions contained 35 mM potassium phosphate, pH 7.6, 1.4 mM dCTP ($\alpha$S), 0.5 mM dGTP, 0.5 mM dATP, 0.5 mM TTP, 0.7 mg/ml bovine serum albumin, 10.2 mM $MgCl_2$, 0.7 mM Tris-HCl (pH 7.9), 3.4 mM KCl, 0.7 mM dithiothreitol, 2% maltitol, 1.34% trehalose, 0.5 $\mu$M P1 primer, 0.5 $\mu$M P2 primer, 150 units of BsiHKCI, and various types and amounts of reverse transcriptase, as noted in FIG. 2. Reactions containing 4 units of AMV Reverse Transcriptase also contained 0.12 units of E. *coli* RNase H (FIG. 2, lanes 1–4). Reactions fractionated in lanes 5–8 of FIG. 2 contained 200 units of MMLV Reverse Transcriptase (MMLV Reverse Transcriptase has intrinsic RNase H activity). The reaction products shown in FIG. 2, lanes 9–12 were generated using 200 units of Superscript II (Superscript II is a proprietary MMLV Reverse Transcriptase lacking endogenous RNase H activity). The reaction products in lanes 2, 6, and 10 of FIG. 2 were produced with approximately $10^6$ molecules of RNA template, not exposed to RNase A. The reaction products in lanes 3, 7, and 11 were produced using approximately $10^6$ molecules, treated with RNase A as described above. Reaction products shown in lanes 4, 8, and 12 of FIG. 2 were generated using approximately 500 molecules of linearized DNA as negative controls. The "products" in lanes 1, 5, and 9 were generated without any form of target nucleic acid sequence, thereby also serving as negative controls.

Reactions were started by mixing 25 $\mu$l of sample (control DNA, RNA template, or water) with 15 $\mu$l of the phosphate buffer containing deoxyribonucleotides and primers to yield a total volume of 40 $\mu$l. The reaction was incubated at 100° C. for 2 minutes. The reaction mixture was cooled to 37° C. for 2 minutes prior to adding 10 $\mu$l of an enzyme mix containing the remaining reaction components, including enzymes as described above, bovine serum albumin, $MgCl_2$, Tris-HCl (pH 7.9), KCl, dithiothreitol, maltitol and trehalose. The samples were then incubated at 37° C. for 30 minutes, followed by 30 minutes at 50° C. All reactions were stopped by heating to 100° C. for 2 minutes. Amplicon was detected by the probe-extension assay previously described. Large amounts of amplicon were observed in lanes 2 and 6 of FIG. 2, generated by reactions containing both reverse transcriptase and RNase H, provided either as an endogenous activity of the particular reverse transcriptase, or exogenously. All RNase A-treated samples failed to produce detectable amplicon. Similarly, reactions lacking target nucleic acid sequence and reactions containing DNA plasmid templates did not support the production of detectable amplicon.

3. Isostatic Amplification

Figure 3:
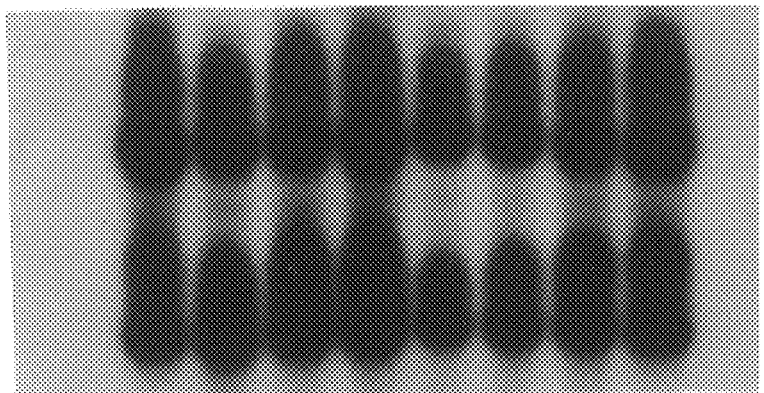
FIG. 3 shows an autoradiogram of gel-fractionated products (Lanes 1–9) from probe-extension assays.

This example demonstrates the substantially isostatic amplification of an RNA template according to the method of the invention. Reactions contained 35 mM potassium phosphate, pH 7.6, 1.4 mM dCTP($\alpha$S), 0.5 mM dATP, 0.5 mM dGTP, 0.5 mM TTP, 0.7 mg/ml bovine serum albumin, 0.7 mM Tris-HCl (pH 7.9), 3.4 mM KCl, 0.7 mM dithiothreitol, 2% maltitol, 1.34% trehalose, 8 units Bst DNA polymerase, 150 units of BsiHKCI, and RNA template. The samples also contained primers P1 and P2, each at 0.5 $\mu$M. RNA-template-containing reactions received 425 pg of RNA transcript template expressed from the 18S rRNA gene of *Cryptosporidium parvum*. The products from these reactions are shown in FIG. 3, lanes 2–9. The "product" shown in FIG. 3, lane 1 is from a control reaction lacking template. The $MgCl_2$ concentration was varied from 7.5 to 12.5 mM (final reaction concentration) for each enzyme that was evaluated, as noted in FIG. 3. AMV-RT reactions received 4 units (FIG. 3, lanes 1 and 2), or 8 units (FIG. 3, lane 9) of enzyme. MMLV-RT-catalyzed reactions received 200 units of reverse transcriptase and no E. *coli* RNase H (FIG. 3, lanes 3–5). Superscript II RT-catalyzed reactions received 200 units of reverse transcriptase and 0.24 units of E. *coli* RNase H (FIG. 3, lanes 6–8).

Reactions were started by mixing either 25 μl of RNA template (FIG. 3, lanes 2–9) or the water-containing control (FIG. 3, lane 1) with 15 μl of phosphate buffer containing deoxyribonucleotides and primers to yield a total volume of 40 μl. The reactions were incubated at 100° C. for 2 minutes. Reactions destined for lanes 3–9 of FIG. 3 were then cooled to 50° C. for 2 minutes; reactions whose products are shown in FIG. 3, lanes 1–2 were cooled to 37° C. for 2 minutes. Subsequently, 10 μl of an enzyme mix containing the remaining reaction components (enzymes as described above, bovine serum albumin, MgCl$_2$, Tris-HCl (pH 7.9), KCl, dithiothreitol, maltitol, and trehalose) was added. Samples examined in FIG. 3, lanes 3–9 were incubated at 50° C. for 60 minutes; samples analyzed in FIG. 3, lanes 1–2 were incubated at 37° C. for 30 minutes, followed by 30 minutes at 50° C. All reactions were stopped by heating to 100° C. for 2 minutes. Amplicon was detected using the probe-extension assay previously described. FIG. 3 shows that amplicon formation was template dependent and that amplicon was found under all substantially isostatic conditions. The substantially isostatic conditions comprised substantially constant temperature and reaction compositions. A substantially constant temperature does not fluctuate during each amplification cycle, although it may vary during the initial few cycles, preferably to facilitate polynucleotide separations or denaturations that may be required prior to the integration of nickable restriction endonuclease recognition sites into polynucleotide fragments containing the segregated copies of the target nucleic acid sequence and its complement. The amount of amplicon produced under substantially isostatic conditions (FIG. 3, lanes 3–9) was comparable to the amplicon found in the two-step temperature reaction using AMV-RT (FIG. 3, lane 2).

4. Sensitivity of the Method of the Invention

The ability of the method of the invention to amplify varying quantities of target nucleic acid sequence to detectable levels was investigated. The reactions contained 35 mM potassium phosphate, pH 7.6, 10.2 mM MgCl$_2$, 1.4 mM dCTP(αS), 0.5 mM dATP, 0.5 mM dGTP, 0.5 mM TTP, 0.7 mg/ml bovine serum albumin, 0.7 mM Tris-HCl (pH 7.9), 3.4 mM KCl, 0.7 mM dithiothreitol, 2% maltitol, 1.34% trehalose, 8 units Bst DNA polymerase, 150 units of BsiHKCI, 0.24 units *E. coli* RNase H, and 8 units AMV reverse transcriptase in final reaction volumes of 50 μl each. The samples also contained primers P1 and P2, each at 0.5 μM, and between $10^0$ to $10^5$ copies of an RNA target nucleic acid sequence in the form of an RNA transcript of the 18S rRNA gene from *Cryptosporidium parvum*, as noted in FIG. 4. RNA copy number was determined as previously described. The concentrated template was diluted in 10 mM Tris-HCl, pH 8.5, and 50 mM KCl.

Figure 4:
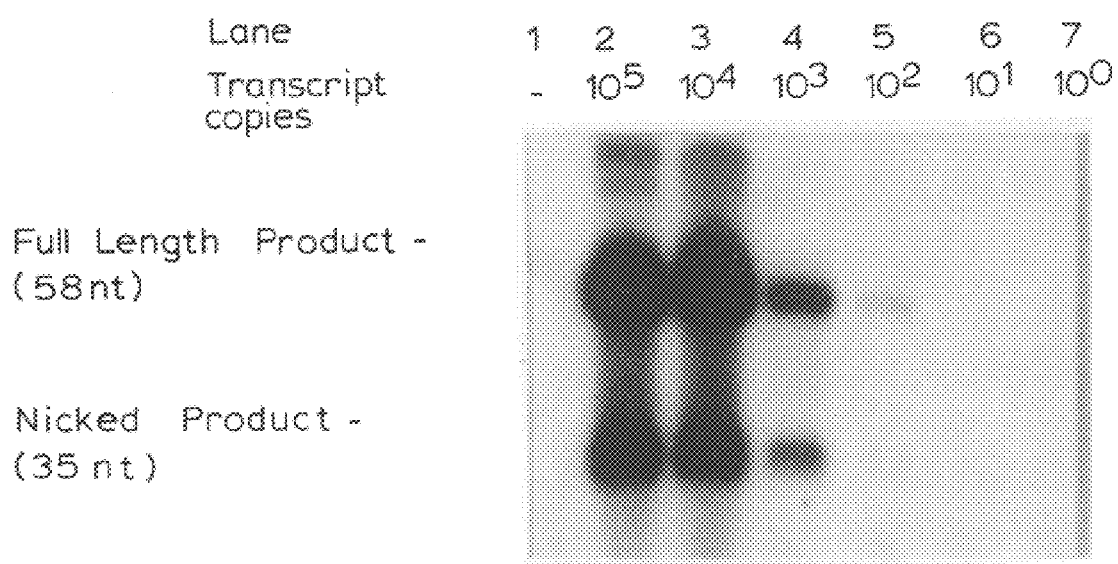
FIG. 4 is an autoradiogram of gel-fractionated products from probe-extension assays measuring amplification products produced as a function of the number of copies of target.

Reactions were started by mixing either 25 μl of RNA template (FIG. 4, lanes 2–7) or the water-containing control (FIG. 4, lane 1) with 15 μl of the phosphate buffer containing the deoxyribonucleotides and primers to yield a total reaction volume of 40 μl. The reactions were incubated at 100° C. for 2 minutes. Reactions were cooled to 50° C. for 2 minutes prior to adding 10 μl of an enzyme mix containing the remaining reaction components (enzymes as described above, bovine serum albumin, MgCl$_2$, Tris-HCl (pH 7.9), KCl, dithiothreitol, maltitol, and trehalose). Reactions were incubated for 60 minutes at 50° C. before stopping the reactions by heating to 100° C. for 2 minutes. Amplicon was detected by the probe-extension assay previously described. The results presented in FIG. 4 show that amplicon was found under all substantially isostatic conditions and detectable amplicon was observed when subjecting as few as 100 copies of the RNA target polynucleotide to the method of the invention (FIG. 4, lane 5).

While the present invention has been described in terms of specific embodiments, it is understood that variations and modifications will occur to those skilled in the art. Accordingly, only those limitations appealing in the appended claims should be placed upon the invention.

What is claimed is:

1. A method for segregating a copy of a target nucleic acid sequence found within a single-stranded polynucleotide, the segregated copy suitable for use in amplifying the target nucleic acid sequence, the method comprising:
  (a) providing a reaction mixture comprising:
    (i) a sample containing or suspected of containing a target nucleic acid sequence positioned within a single-stranded polynucleotide at other than an end of said polynucleotide;
    (ii) a first polymerizing enzyme which polymerizes deoxyribonucleoside triphosphates by extending a hybridized primer, using the single strand of said polynucleotide as a template, and a second polymerizing enzyme which polymerizes deoxyribonucleoside triphosphates by extending a hybridized primer and further which displaces a strand, with the proviso that when the target nucleic acid is a DNA, the first polymerizing enzyme is optionally the same as the second polymerizing enzyme;
    (iii) a mixture of deoxyribonucleoside triphosphates that includes a modified deoxyribonucleoside triphosphate; and
    (iv) a first amplification primer which hybridizes to the target nucleic acid sequence and forms a hybridized primer therewith, the first amplification primer comprising an oligodeoxyribonucleotide having a 3' end and a 5' end, the 3' end of said first amplification primer being complementary to the 3' end of said target nucleic acid sequence, the 5' end of said first amplification primer having a first recognition sequence for a first restriction endonuclease that is capable of nicking one strand of a double-stranded hemi-modified recognition site for said first restriction endonuclease; and
    (v) a second amplification primer comprising an oligodeoxyribonucleotide having a 3' end and a 5' end, the 3' end of said second amplification primer being complementary to the 3' end of the complement of said target nucleic acid sequence and which hybridizes thereto, the 5' end of said second amplification primer having a second recognition sequence for a second restriction endonuclease that is capable of nicking one strand of a double-stranded hemi-modified recognition site for said second restriction endonuclease;
  (b) subjecting the reaction mixture to a means for separating any double-stranded nucleic acid in the reaction mixture into single strands which means is a RNase enzyme; and
  (c) allowing the reaction mixture sufficient time for hybridization, primer extension, and nicking to occur, whereby there is produced a double-stranded polynucleotide extension product suitable for amplification comprising a segregated copy of said target nucleic acid sequence and a segregated copy of the complement of said target nucleic acid sequence, said double-stranded polynucleotide extension product being defined at opposing ends by a first nickable restriction site and a second nickable restriction site for said first and second restriction endonucleases, respectively.

2. A method for segregating a copy of a target nucleic acid sequence found within a single-stranded polynucleotide, the segregated copy suitable for use in amplifying the target nucleic acid sequence, the method comprising:
  (a) hybridizing a first amplification primer to the 3' end of a target nucleic acid sequence within a single-stranded polynucleotide fragment to form a hybridized first amplification primer, said first amplification primer comprising an oligodeoxyribonucleotide having a 3' end and a 5' end, the 3' end of said first amplification primer being complementary to the 3' end of said target nucleic acid sequence, the 5' end of said first amplification primer having a first recognition sequence for a first restriction endonuclease that is capable of nicking one strand of a double-stranded hemi-modified recognition site for said first restriction endonuclease;

(b) extending the hybridized first amplification primer along its 3' end in the presence of deoxyribonucleoside triphosphates, a modified deoxyribonucleoside triphosphate, and a first polymerizing enzyme which polymerizes deoxyribonucleoside triphosphates using the target nucleic acid sequence as a template to produce a first double-stranded polynucleotide having a first modified polynucleotide extension product that is complementary and bound to said single-stranded polynucleotide;

(c) enzymatically separating said single-stranded polynucleotide from the first modified polynucleotide extension product;

(d) hybridizing a second amplification primer to an internal site on said first modified polynucleotide extension product to form a hybridized second amplification primer, said second amplification primer comprising an oligodeoxyribonucleotide having a 3' end and a 5' end, the 3' end of said second amplification primer being complementary to the 3' end of the complement of said target nucleic acid sequence and hybridizing thereto, the 5' end of said second amplification primer having a second recognition sequence for a second restriction endonuclease that is capable of nicking one strand of a double-stranded hemi-modified recognition site for the second restriction endonuclease;

(e) extending the hybridized second amplification primer along its 3' end in a reaction mixture comprising a mixture of deoxyribonucleoside triphosphates, a modified deoxyribonucleoside triphosphate, and a second polymerizing enzyme which polymerizes deoxyribonucleoside triphosphates in the presence of a polynucleotide template and which displaces a strand, to produce a second double-stranded polynucleotide comprising a second modified polynucleotide extension product that is hybridized to the first modified polynucleotide extension product, the second modified polynucleotide extension product comprising a copy of said target nucleic acid sequence segregated from the single-stranded polynucleotide and positioned at opposing ends between said second recognition sequence and the complement of said first recognition sequence, said first recognition sequence on the first modified polynucleotide extension product and the complement of said first recognition sequence on the second polynucleotide extension product forming a double-stranded hemi-modified recognition site for said first restriction endonuclease; and (f) nicking one strand of said double-stranded hemi-modified recognition site for said first restriction endonuclease in the presence of said first restriction endonuclease, deoxyribonucleoside triphosphates, a modified deoxyribonucleoside triphosphate, and said second polymerizing enzyme, whereby the 3' end produced by the nick is extended, thereby displacing any portion of said first modified polynucleotide extension product downstream therefrom and forming a third double-stranded polynucleotide comprising a segregated copy of said target nucleic acid sequence that is hybridized to a segregated copy of the complement of said target nucleic acid sequence, the third double-stranded polynucleotide being defined at opposing ends by said first nickable recognition site and a second nickable recognition site for said first and second restriction endonucleases, respectively.

3. The method according to claim 1 wherein the reaction mixture is an aqueous or substantially aqueous medium.

4. The method according to claim 1 or 2 wherein said target nucleic acid sequence is RNA.

5. The method according to claim 2 wherein said steps are conducted in the presence of at least one of maltitol, trehalose, tetramethylammonium chloride, and tetraethylammonium chloride.

6. The method according to claim 2 wherein said separating step (c) comprises introducing an RNAse activity.

7. The method according to claim 6 wherein said RNase activity is an RNase H activity.

8. The method according to claim 3 wherein said first restriction endonuclease is selected from the group consisting of AccI, AlwI, AvaI, BsaI, BsiHKCI, BsmI, BsoBI, BsrI, BstXI, DpnI, Fnu4HI, FokI, HincII, HindII, HphI, MspI, NciI, NlaIV, NspI, PflMI, and Tth111I.

9. The method according to claim 8 wherein said first restriction endonuclease is BsiHKCI.

10. The method according to claim 3 wherein said second restriction endonuclease is selected from the group consisting of AccI, AlwI, AvaI, BsaI, BsiHKCI, BsmI, BsoBI, BsrI, BstXI, DpnI, Fnu4HI, FokI, HincII, HindII, HphI, MspI, NciI, NlaIV, NspI, PflMI, and Tth111I.

11. The method according to claim 10 wherein said second restriction endonuclease is BsiHKCI.

12. The method according to claim 3 wherein said first restriction endonuclease and said second restriction endonuclease are the same.

13. The method according to claim 12 wherein said first nickable recognition site and said second nickable recognition site are the same.

14. The method according to claim 3 wherein said modified deoxyribonucleoside triphosphate is selected from the group consisting of 2'-deoxyguanosine 5'-O-(1-thiotriphosphate), 2'-deoxyadenosine 5'-O-(1-thiotriphosphate), thymidine 5'-O-(1-thiotriphosphate), 2'-deoxycytidine 5'-O-(1-thiotriphosphate), 2'-deoxyuridine 5'-triphosphate, 5-methyldeoxycytidine 5'-triphosphate, and 7-deaza-2'-deoxyguanosine 5'-triphosphate.

15. The method according to claim 3 wherein said first polymerizing enzyme is a polymerase.

16. The method according to claim 15 wherein said first polymerizing enzyme has reverse transcriptase activity.

17. The method according to claim 3 wherein said second polymerizing enzyme is a DNA polymerase.

18. The method according to claim 17 wherein said second polymerizing enzyme is selected from the group consisting of Bst DNA polymerase, Taq DNA polymerase, Tth DNA polymerase, Tfl DNA polymerase, $E.$ $coli$ DNA polymerase, $E.$ $coli$ DNA polymerase Klenow fragment, and exo$^-$ $E.$ $coli$ DNA polymerase Klenow fragment.

19. The method according to claim 18 wherein said second polymerizing enzyme is Bst DNA polymerase.

20. The method according to claim 3 wherein said first polymerizing enzyme and said second polymerizing enzyme are the same.

21. A kit for carrying out a method for segregating a copy of a target nucleic acid sequence found within a single-stranded polynucleotide comprising:

(a) a polymerizing enzyme capable of polymerizing deoxyribonucleoside triphosphates to generate a first product consisting essentially of a complement of a template, said enzyme being capable of strand displacement;

(b) a pair of primers comprising a first amplification primer and a second amplification primer, said first amplification primer having a 3' end that is complementary to the 3' end of a target nucleic acid sequence that is positioned within a larger polynucleotide at a location other than a terminus, and a 5' end that includes a first recognition sequence for a first restriction endonuclease capable of nicking a hemi-modified first recognition site, said second amplification primer having a 3' end that is complementary to the 3' end of the complement of the target nucleic acid sequence and a 5' end that includes a second recognition sequence for a second restriction endonuclease capable of nicking a hemi-modified second recognition site;

(c) from one to two restriction endonucleases capable of nicking a substantially hemi-modified restriction endonuclease recognition site;

(d) deoxyribonucleoside triphosphates;

(e) a modified deoxyribonucleoside triphosphate and (f) an enzyme having RNAse activity.

22. The kit according to claim 21 wherein said polymerizing enzyme is selected from the group consisting of Avian Myeloblastosis Virus Reverse Transcriptase, Moloney Murine Leukemia Virus Reverse Transcriptase, SuperScript II, Bst DNA polymerase, Taq DNA polymerase, Tth DNA polymerase, Tfl DNA polymerase, E. coli DNA polymerase Klenow fragment, and exo⁻ E. coli DNA polymerase Klenow fragment.

23. The kit according to claim 21 wherein said restriction endonucleases are selected from the group consisting of AccI, AlwI, AvaI, BsaI, BsiHKCI, BsmI, BsoBI, BsrI, BstXI, DpnI, Fnu4HI, FokI, HincII, HindII, HphI, MspI, NciI, NlaIV, NspI, PflMI, and Tth111I.

24. The kit according to claim 23 wherein said restriction endonucleases are BsiHKCI.

25. A method for amplifying a copy of a target nucleic acid sequence found within a single-stranded polynucleotide, the method comprising:

(a) providing a reaction mixture comprising:
  (i) a sample containing or suspected of containing a target nucleic acid sequence positioned within a single-stranded polynucleotide at other than an end of said polynucleotide;
  (ii) a first polymerizing enzyme which polymerizes deoxyribonucleoside triphosphates by extending a hybridized primer, using the single strand of said polynucleotide as a template, and a second polymerizing enzyme which polymerizes deoxyribonucleoside triphosphates by extending a hybridized primer and further which displaces a strand with the proviso that when the target nucleic acid is a DNA, the first polymerizing enzyme is optionally the same as the second polymerizing enzyme;
  (iii) a mixture of deoxyribonucleoside triphosphates that includes a modified deoxyribonucleoside triphosphate;
  (iv) a first amplification primer which hybridizes to the target nucleic acid sequence and forming a hybridized primer therewith, the first amplification primer comprising an oligodeoxyribonucleotide having a 3' end and a 5' end, the 3' end of said first amplification primer being complementary to the 3' end of said target nucleic acid sequence, the 5' end of said first amplification primer having a first recognition sequence for a first restriction endonuclease that is capable of nicking one strand of a double-stranded hemi-modified recognition site for said first restriction endonuclease; and
  (v) a second amplification primer comprising an oligodeoxyribonucleotide having a 3' end and a 5' end, the 3' end of said second amplification primer being complementary to the 3' end of the complement of said target nucleic acid sequence and hybridizing thereto, the 5' end of said second amplification primer having a second recognition sequence for a second restriction endonuclease that is capable of nicking one strand of a double-stranded hemi-modified recognition site for said second restriction endonuclease;

(b) subjecting the reaction mixture to a means for separating any double-stranded nucleic acid in the reaction mixture into single strands which means is a RNase enzyme;

(c) allowing the reaction mixture sufficient time for hybridization, primer extension, and nicking to occur, whereby there is produced a double-stranded polynucleotide extension product suitable for amplification comprising a segregated copy of said target nucleic acid sequence and a segregated copy of the complement of said target nucleic acid sequence, said double-stranded polynucleotide extension product being defined at opposing ends by a first nickable restriction site and a second nickable restriction site for said first and second restriction endonucleases, respectively;

(d) amplifying the segregated copy of the target nucleic acid sequence or its complement by contacting the double-stranded polynucleotide extension product with said first restriction endonuclease and said second restriction endonuclease in the presence of a mixture of an enzyme having a DNA polymerase activity that is capable of strand displacement, deoxyribonucleoside triphosphates, and a modified deoxyribonucleoside triphosphate, whereby said first and second recognition sequences of said first and said second recognition sites are nicked and the 3' ends of the sites that are nicked are extended, generating a nascent target nucleic acid sequence or its complement, and displacing the downstream copy of the target nucleic acid sequence or its complement in the process; and (e) allowing step (d) to continue for a sufficient time to produce a detectable amount of the segregated copies of the target nucleic acid sequence.

26. A method for amplifying a copy of a target nucleic acid sequence found within a single-stranded polynucleotide, the method comprising:

(a) hybridizing a first amplification primer to the 3' end of a target nucleic acid sequence within a single-stranded polynucleotide to form a hybridized first amplification primer, said first amplification primer comprising an oligodeoxyribonucleotide having a 3' end and a 5' end, the 3' end of said first amplification primer being complementary to the 3' end of said target nucleic acid sequence, the 5' end of said first amplification primer having a first recognition sequence for a first restriction endonuclease that is capable of nicking one strand of a double-stranded hemi-modified recognition site for said first restriction endonuclease;

(b) extending the hybridized first amplification primer along its 3' end in the presence of deoxyribonucleoside triphosphates, a modified deoxyribonucleoside triphosphate, and a first polymerizing enzyme which polymerizes deoxyribonucleoside triphosphates using the target nucleic acid sequence as a template to produce a first double-stranded polynucleotide having a first modified polynucleotide extension product that is complementary and bound to said single-stranded polynucleotide;

(c) enzymatically separating said single-stranded polynucleotide from the first modified polynucleotide extension product;

(d) hybridizing a second amplification primer to an internal site on said first modified polynucleotide extension product to form a hybridized second amplification primer, said second amplification primer comprising an oligodeoxyribonucleotide having a 3' end and a 5' end, the 3' end of said second amplification primer being complementary to the 3' end of the complement of said target nucleic acid sequence and which hybridizes thereto, the 5' end of said second amplification primer having a second recognition sequence for a second restriction endonuclease that is capable of nicking one strand of a double-stranded hemi-modified recognition site for the second restriction endonuclease;

(e) extending the hybridized second amplification primer along its 3' end in a reaction mixture comprising a mixture of deoxyribonucleoside triphosphates, a modified deoxyribonucleoside triphosphate, and a second polymerizing enzyme which polymerizes deoxyribonucleoside triphosphates in the presence of a polynucleotide template and which displaces a strand, to produce a second double-stranded polynucleotide comprising a second modified polynucleotide extension product that is hybridized to the first modified polynucleotide extension product, the second modified polynucleotide extension product comprising a copy of said target nucleic acid sequence segregated from the single-stranded polynucleotide and positioned at opposing ends between said second recognition sequence and the complement of said first recognition sequence, said first recognition sequence on the first modified polynucleotide extension product and the complement of said first recognition sequence on the second polynucleotide extension product forming a double-stranded hemi-modified recognition site for said first restriction endonuclease;

(f) nicking one strand of said double-stranded hemi-modified recognition site for said first restriction endonuclease in the presence of said first restriction endonuclease, deoxyribonucleoside triphosphates, a modified deoxyribonucleoside triphosphate, and said second polymerizing enzyme, whereby the 3' end produced by the nick is extended, thereby displacing any portion of said first modified polynucleotide extension product downstream therefrom and forming a third double-stranded polynucleotide comprising a segregated copy of said target nucleic acid sequence that is hybridized to a segregated copy of the complement of said target nucleic acid sequence, the third double-stranded polynucleotide being defined at opposing ends by said first nickable recognition site and a second nickable recognition site for said first and second restriction endonucleases, respectively;

(g) amplifying the segregated copy of the target nucleic acid sequence or its complement by contacting the third double-stranded polynucleotide with said first restriction endonuclease and said second restriction endonuclease in the presence of a mixture of an enzyme having a DNA polymerase activity that is capable of strand displacement, deoxyribonucleoside triphosphates, and a modified deoxyribonucleoside triphosphate, whereby said first and second recognition sequences of said first and said second recognition sites are nicked and the 3' ends of the sites that are nicked are extended, generating a nascent target nucleic acid sequence or its complement, and displacing the downstream copy of the target nucleic acid sequence or its complement in the process; and (h) allowing step (g) to continue for a sufficient time to produce a detectable amount of the segregated copies of the target nucleic acid sequence.

27. A method for determining the presence of a target nucleic acid sequence found within a single-stranded polynucleotide, the method comprising:

(a) providing a reaction mixture comprising:
  (i) a sample containing or suspected of containing a target nucleic acid sequence positioned within a single-stranded polynucleotide at other than an end of said polynucleotide;
  (ii) a first polymerizing enzyme which polymerizes deoxyribonucleoside triphosphates by extending a hybridized primer, using the single strand of said polynucleotide as a template, and a second polymerizing enzyme which polymerizes deoxyribonucleoside triphosphates by extending a hybridized primer and further which displaces a strand, with the proviso that when the target nucleic acid is a DNA, the first polymerizing enzyme is optionally the same as the second polymerizing enzyme;
  (iii) a mixture of deoxyribonucleoside triphosphates that includes a modified deoxyribonucleoside triphosphate; and
  (iv) a first amplification primer which hybridizes to the target nucleic acid and forming a hybridized primer therewith, the first amplification primer comprising an oligodeoxyribonucleotide having a 3' end and a 5' end, the 3' end of said first amplification primer being complementary to the 3' end of said target nucleic acid sequence, the 5' end of said first amplification primer having a first recognition sequence for a first restriction endonuclease that is capable of nicking one strand of a double-stranded hemi-modified recognition site for said first restriction endonuclease; and
  (v) a second amplification primer comprising an oligodeoxyribonucleotide having a 3' end and a 5' end, the 3' end of said second amplification primer being complementary to the 3' end of the complement of said target nucleic acid sequence and which hybridizes thereto, the 5' end of said second amplification primer having a second recognition sequence for a second restriction endonuclease that is capable of nicking one strand of a double-stranded hemi-modified recognition site for said second restriction endonuclease;

(b) subjecting the reaction mixture to a means for separating any double-stranded nucleic acid in the reaction mixture into single strands which means is a RNase enzyme;

(c) allowing the reaction mixture sufficient time for hybridization, primer extension, and nicking to occur, whereby there is produced a double-stranded polynucleotide extension product suitable for amplification comprising a segregated copy of said target nucleic acid sequence and a segregated copy of the complement of said target nucleic acid sequence, said double-stranded polynucleotide extension product being defined at opposing ends by a first nickable restriction site and a second nickable restriction site for said first and second restriction endonucleases, respectively;

(d) amplifying the segregated copy of the target nucleic acid sequence or its complement by contacting the double-stranded polynucleotide extension product with said first restriction endonuclease and said second restriction endonuclease in the presence of a mixture of an enzyme having a DNA polymerase activity and capable of strand displacement, deoxyribonucleoside triphosphates, and a modified deoxyribonucleoside triphosphate, whereby said first and second recognition sequences of said first and said second recognition sites are nicked and the 3' ends of the sites that are nicked are extended, generating a nascent target nucleic acid sequence or its complement, and displacing the downstream copy of the target nucleic acid sequence or its complement in the process;

(e) allowing step (d) to continue for a sufficient time to produce a detectable amount of the segregated copies of the target nucleic acid sequence; and (f) determining the presence of a detectable amount of the segregated copies of the target nucleic acid sequence.

28. A method for determining the presence of a target nucleic acid sequence found within a single-stranded polynucleotide, the method comprising:

(a) hybridizing a first amplification primer to the 3' end of a target nucleic acid sequence within a single-stranded polynucleotide to form a hybridized first amplification primer, said first amplification primer comprising an oligodeoxyribonucleotide having a 3' end and a 5' end, the 3' end of said first amplification primer being complementary to the 3' end of said target nucleic acid sequence, the 5' end of said first amplification primer having a first recognition sequence for a first restriction endonuclease that is capable of nicking one strand of a double-stranded hemi-modified recognition site for said first restriction endonuclease;

(b) extending the hybridized first amplification primer along its 3' end in the presence of deoxyribonucleoside triphosphates, a modified deoxyribonucleoside triphosphate, and a first polymerizing enzyme which polymerizes deoxyribonucleoside triphosphates using the target nucleic acid sequence as a template to produce a first double-stranded polynucleotide having a first modified polynucleotide extension product that is complementary and bound to said single-stranded polynucleotide;

(c) enzymatically separating said single-stranded polynucleotide from the first modified polynucleotide extension product;

(d) hybridizing a second amplification primer to an internal site on said first modified polynucleotide extension product to form a hybridized second amplification primer, said second amplification primer comprising an oligodeoxyribonucleotide having a 3' end and a 5' end, the 3' end of said second amplification primer being complementary to the 3' end of the complement of said target nucleic acid sequence and which hybridizes thereto, the 5' end of said second amplification primer having a second recognition sequence for a second restriction endonuclease that is capable of nicking one strand of a double-stranded hemi-modified recognition site for the second restriction endonuclease;

(e) extending the hybridized second amplification primer along its 3' end in a reaction mixture comprising a mixture of deoxyribonucleoside triphosphates, a modified deoxyribonucleoside triphosphate, and a second polymerizing enzyme which polymerizes deoxyribonucleoside triphosphates in the presence of a polynucleotide template and which displaces a strand, to produce a second double-stranded polynucleotide comprising a second modified polynucleotide extension product that is hybridized to the first modified polynucleotide extension product, the second modified polynucleotide extension product comprising a copy of said target nucleic acid sequence segregated from the single-stranded polynucleotide and positioned at opposing ends between said second recognition sequence and the complement of said first recognition sequence, said first recognition sequence on the first modified polynucleotide extension product and the complement of said first recognition sequence on the second polynucleotide extension product forming a double-stranded hemi-modified recognition site for said first restriction endonuclease;

(f) nicking one strand of said double-stranded hemi-modified recognition site for said first restriction endonuclease in the presence of said first restriction endonuclease, deoxyribonucleoside triphosphates, a modified deoxyribonucleoside triphosphate, and said second polymerizing enzyme, whereby the 3' end produced by the nick is extended, thereby displacing any portion of said first modified polynucleotide extension product downstream therefrom and forming a third double-stranded polynucleotide comprising a segregated copy of said target nucleic acid sequence that is hybridized to a segregated copy of the complement of said target nucleic acid sequence, the third double-stranded polynucleotide being defined at opposing ends by said first nickable recognition site and a second nickable recognition site for said first and second restriction endonucleases, respectively;

(g) amplifying the segregated copy of the target nucleic acid sequence or its complement by contacting the third double-stranded polynucleotide with said first restriction endonuclease and said second restriction endonuclease in the presence of a mixture of an enzyme having a DNA polymerase activity that is capable of strand displacement, deoxyribonucleoside triphosphates, and a modified deoxyribonucleoside triphosphate, whereby said first and second recognition sequences of said first and said second recognition sites are nicked and the 3' ends of the sites that are nicked are extended, generating a nascent target nucleic acid sequence or its complement, and displacing the downstream copy of the target nucleic acid sequence or its complement in the process;

(h) allowing step (g) to continue for a sufficient time to produce a detectable amount of the segregated copies of the target nucleic acid sequence; and (i) determining the presence of a detectable amount of the segregated copies of the target nucleic acid sequence.

29. The method according to claim 26 wherein said amplifying step (g) and said allowing step (h) occur under substantially isothermal conditions.

30. The method according to claim 29 wherein said amplifying step (g) and said allowing step (h) occur from about 37° C. to about 60° C.

31. The method according to claim 30 wherein said amplifying step (g) and said allowing step (h) occur at a temperature of about 60° C.

32. The method according to claim 1 wherein said RNase activity is an RNase H activity.

* * * * *